US006615824B2

(12) United States Patent
Power

(10) Patent No.: US 6,615,824 B2
(45) Date of Patent: Sep. 9, 2003

(54) APPARATUS AND METHODS FOR THE DELIVERY OF MEDICAMENTS TO THE RESPIRATORY SYSTEM

(75) Inventor: John S. Power, Moycullen (IE)

(73) Assignee: Aerogen, Inc., Mountain View, CA (US)

(*) Notice: Subject to any disclaimer, the term of this patent is extended or adjusted under 35 U.S.C. 154(b) by 0 days.

(21) Appl. No.: 09/849,194

(22) Filed: May 4, 2001

(65) Prior Publication Data

US 2002/0002975 A1 Jan. 10, 2002

(30) Foreign Application Priority Data

May 5, 2000 (IE) .................................. PCT/IE00/00051

(51) Int. Cl.[7] ............................................... A61M 11/00

(52) U.S. Cl. ............................ 128/200.14; 128/200.21; 128/200.23; 128/200.16; 128/204.18; 128/204.21; 239/338

(58) Field of Search ........................ 128/200.14, 200.21, 128/200.23, 200.16, 204.18, 204, 21, 202.22, 204.23, 202.27; 239/338, 102.2; 222/180

(56) References Cited

U.S. PATENT DOCUMENTS

| | | | | | |
|---|---|---|---|---|---|
| 3,561,444 | A | * | 2/1971 | Boucher | 128/200.16 |
| 3,903,884 | A | | 9/1975 | Huston et al. | |
| 4,030,492 | A | | 6/1977 | Simburner | |
| 4,076,021 | A | | 2/1978 | Thompson | |
| 4,566,452 | A | | 1/1986 | Farr | |
| 4,805,609 | A | * | 2/1989 | Roberts et al. | 128/200.21 |
| 4,819,629 | A | * | 4/1989 | Jonson | 128/203.22 |
| 5,007,419 | A | * | 4/1991 | Weinstein et al. | 128/200.23 |
| 5,022,587 | A | | 6/1991 | Hochstein | |
| 5,063,922 | A | | 11/1991 | Häkkinen | |
| 5,080,093 | A | * | 1/1992 | Raabe et al. | 128/203.12 |
| 5,164,740 | A | | 11/1992 | Ivri | |
| 5,230,496 | A | | 7/1993 | Shillington et al. | |
| 5,355,872 | A | | 10/1994 | Riggs et al. | |
| 5,357,946 | A | | 10/1994 | Kee et al. | |
| 5,388,571 | A | | 2/1995 | Roberts et al. | |
| 5,445,141 | A | | 8/1995 | Kee et al. | |
| 5,479,920 | A | * | 1/1996 | Piper et al. | 128/204.23 |
| 5,584,285 | A | * | 12/1996 | Salter et al. | 128/200.21 |
| 5,586,550 | A | | 12/1996 | Ivri et al. | |
| 5,588,166 | A | | 12/1996 | Burnett | |
| 5,666,946 | A | | 9/1997 | Langenback | |
| 5,752,502 | A | | 5/1998 | King | |
| 5,758,637 | A | | 6/1998 | Ivri et al. | |

(List continued on next page.)

FOREIGN PATENT DOCUMENTS

| | | |
|---|---|---|
| EP | 0933138 A2 | 8/1999 |
| WO | WO 97/07896 | 3/1997 |
| WO | WO 99/63946 | 12/1999 |
| WO | WO 01/18280 | 3/2001 |

OTHER PUBLICATIONS

Fink, James B. et al., Clinical Practice in Respiratory Care, Aerosol Drug Therapy, Chapter 12, pp. 308–342, 1999.

*Primary Examiner*—Ehud Gartenberg
*Assistant Examiner*—Azadeh Kokabi
(74) *Attorney, Agent, or Firm*—Townsend and Townsend and Crew LLP

(57) ABSTRACT

An apparatus for delivery of a medicament to the respiratory system comprises a reservoir that is adapted to hold a liquid medicament that is to be delivered to a respiratory system. An aerosol generator is provided that is adapted to aerosolize the liquid medicament. A liquid supplier is used to deliver the liquid medicament from the reservoir to the aerosol generator. A connector is operably coupled to the aerosol generator and comprises a gas conduit having an inlet, and an outlet, and an aerosol supply conduit. The aerosol generator is configured to provide the aerosolized liquid medicament into the gas conduit through the aerosol supply conduit, and the gas conduit is adapted to pass gases to entrain the aerosolized liquid medicament.

88 Claims, 19 Drawing Sheets

U.S. PATENT DOCUMENTS

| | | | | |
|---|---|---|---|---|
| 5,788,665 | A | 8/1998 | Sekins | |
| 5,823,179 | A | * 10/1998 | Grychowski et al. | 128/200.18 |
| 5,829,723 | A | 11/1998 | Brunner et al. | |
| 5,862,802 | A | 1/1999 | Bird | |
| 5,938,117 | A | 8/1999 | Ivri | |
| 6,000,396 | A | 12/1999 | Melker et al. | |
| 6,014,970 | A | 1/2000 | Ivri et al. | |
| 6,029,666 | A | 2/2000 | Aloy et al. | |
| 6,182,662 | B1 | 2/2001 | McGhee | |
| 6,205,999 | B1 | 3/2001 | Ivri et al. | |
| 6,235,177 | B1 | 5/2001 | Borland et al. | |

* cited by examiner

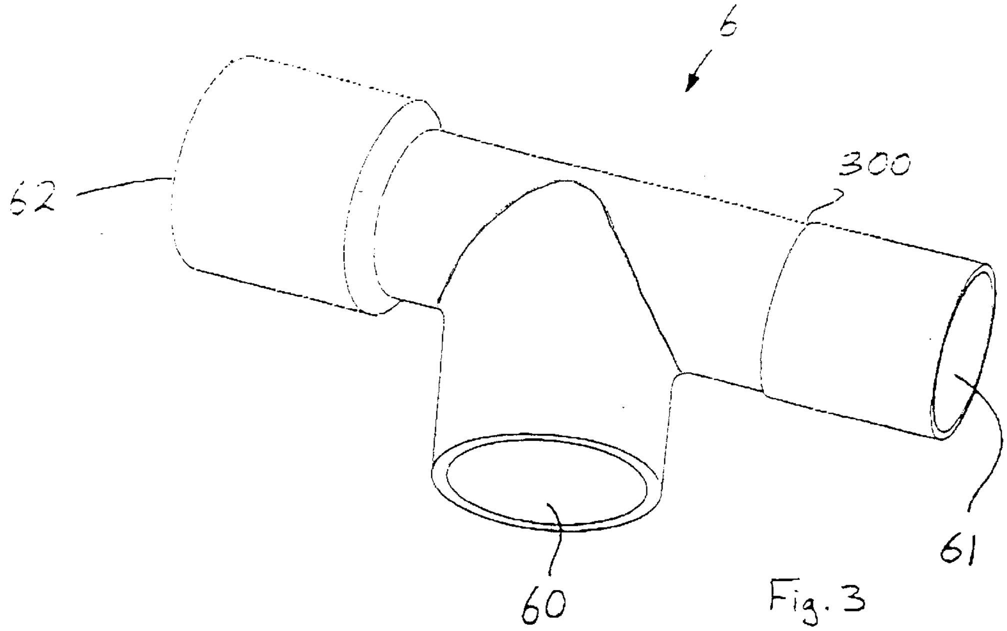
Fig. 3
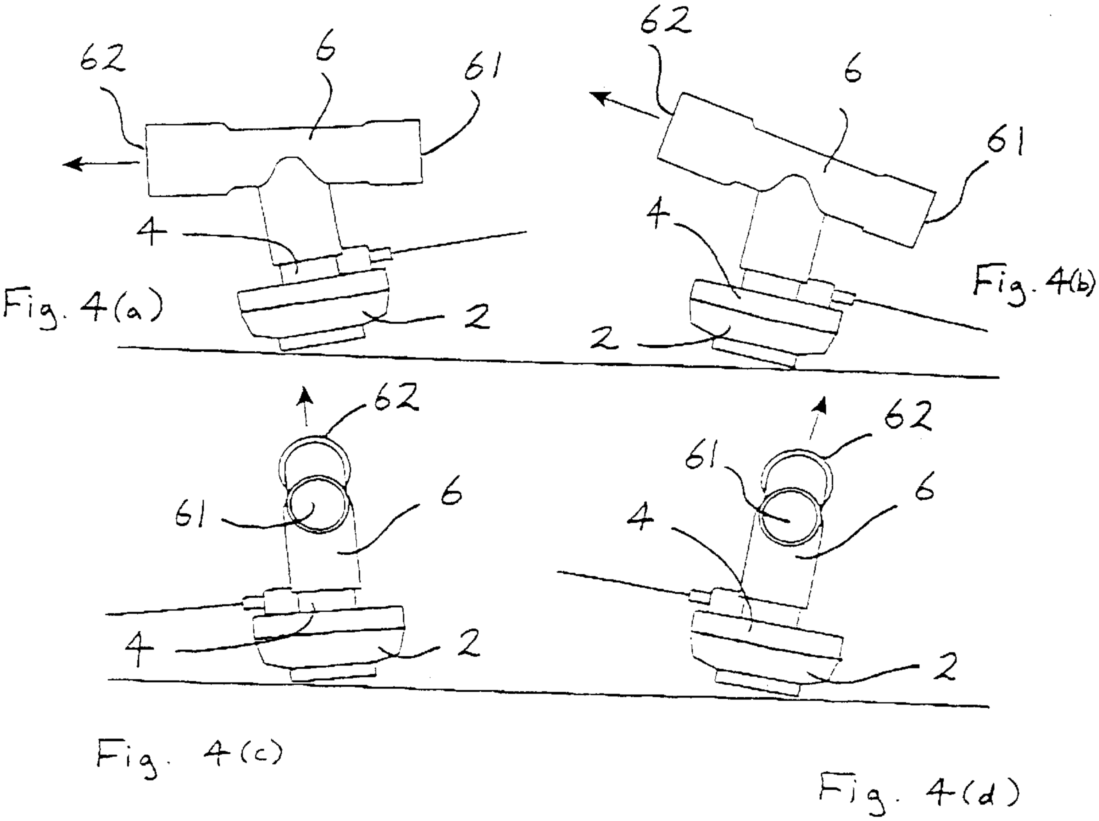
Fig. 4(a)
Fig. 4(b)
Fig. 4(c)
Fig. 4(d)

APPARATUS AND METHODS FOR THE DELIVERY OF MEDICAMENTS TO THE RESPIRATORY SYSTEM

CROSS-REFERENCES TO RELATED APPLICATIONS

This application claims priority from PCT/IE/00051 filed on May 5, 2000, the complete disclosure of which is incorporated herein by reference.

BACKGROUND OF THE INVENTION

This invention relates to methods and apparatus for delivery of medicament to the respiratory system of a patient. In particular, the invention relates to apparatus and methods of this type for use in association with a nebulizer.

It is known to use a nebulizer to create an aerosol of medication for delivery into the respiratory system of a patient. Typically the medication is placed in a cup which is held over a reservoir of buffer water. A piezoelectric element is vibrated ultrasonically under the buffer water transferring energy to the water, thus causing an aerosol to be formed in the medication cup. Baffles are provided between the medication cup and the airway in an attempt to ensure large particles of medication rain out on the filter and drip back down into the medication cup.

These nebulizers suffer from a number of disadvantages. In particular, medications have a range of different viscosities, however particle generation is not consistent across the range. Thus the medication particle size is not accurately controlled and a broad range of particles pass into the patient airway. Nebulized medication which rains out on the filter drips back into the cup only to be nebulized again. This may degrade or destroy the medication.

The medication in the cup is directly exposed to the airway. Therefore the nebulizer must be maintained substantially horizontal at all times to prevent medication spilling out into the patient airway. Also the ventilator pressure will be lost when the medication cup is removed to refill it.

This method of aerosol generation requires a relatively large amount of energy, the response time of aerosol generation is thus large. A considerable amount of heat is generated during use of the nebulizer, therefore to prevent patient discomfort or injury the nebulizer is placed away from the patient. However this necessitates a long inhalation tube between the nebulizer and the patient, increasing drug loss through rain out along the inhalation tube, and further increasing the response time to patient inspiration. Further, the generated heat degenerates the medication, which can be particularly harmful to protein based drugs.

Hence, this invention is related to apparatus and techniques for delivery of medicament to the respiratory system of a patient.

BRIEF SUMMARY OF THE INVENTION

In one embodiment, an apparatus for delivery of medicament to the respiratory system comprises a reservoir, such as a medication cup, for receiving a liquid medication that is to be delivered to a respiratory system. The apparatus also includes an aerosol generator that may be held within a housing. A liquid supplier is provided to deliver the liquid medicament from the cup to the aerosol generator. A connector is employed to receive aerosol generated by the aerosol generator. The connector has an aerosol inlet for receiving aerosol from the generator, an air inlet, and an outlet. In this way, the aerosol that is received through the aerosol inlet may be entrained with a gas passing through the air inlet, and the entrained aerosol may pass through the outlet for delivery to a patient. Conveniently, the connector may be coupled to a ventilator to introduce the gas into the air inlet.

In one aspect, the connector is of generally T-shape and has an inlet leg with a longitudinal axis and an outlet leg with an air inlet end and an aerosol outlet end. The inlet is connected to the outlet leg intermediate the air inlet end and the aerosol outlet end, and the outlet leg has a first portion extending from the air inlet end to the connection to the inlet leg. The first portion has a longitudinal axis, with the longitudinal axis of the inlet leg subtending an angle of less than 90° with the longitudinal axis of the first portion of the outlet leg. Preferably the angle between the longitudinal axis of the first portion of the outlet leg and the longitudinal axis of the inlet leg is less than 80°. Ideally the angle between the longitudinal axis of the first portion of the outlet leg and the longitudinal axis of the inlet leg is about 75°. In some cases, the outlet leg may have a second portion extending from the first portion, the second portion being substantially in line with the first portion.

Conveniently, the connector may also be defined in terms of a gas conduit having an inlet, and an outlet, and an aerosol supply conduit. With such a configuration, the aerosol generator is configured to provide the aerosolized liquid medicament into the gas conduit through the aerosol supply conduit, and the gas conduit is adapted to pass gases to entrain the aerosolized liquid medicament.

In another embodiment of the invention, the medication cup is releasably mounted to the aerosol generator housing. In one aspect, the medication cup has a reservoir for holding a medication and a delivery tube having an inlet for receiving medication from the reservoir. The delivery tube is associated with the liquid supplier to deliver the liquid medication to the aerosol generator. The inlet may comprise a number of inlet slots which are circumferentially spaced-apart around the delivery tube.

The aerosol generator housing and the medication cup may be configured to be sealed to each other. This may be accomplished using a sealing mechanism, such as a skirt extending from the aerosol generator housing to sealingly engage the medication cup. Conveniently, the skirt may have an angled surface to sealingly engage a chamfered mouth of the medication cup. In a further aspect, the liquid supplier may be mounted to the aerosol generator housing.

In a further embodiment, the medication cup has a base with support for supporting the cup in an upright orientation when receiving liquid medication. The support may comprise a support skirt extending from the base of the cup. Conveniently, the medication cup may include a central well from which the delivery tube extends.

In one embodiment, the apparatus includes controller for controlling the operation of the aerosol generator. For example, the controller may send control signals to actuate the aerosol generator just prior to initiating an inhalation cycle of a ventilator and to deactivate the aerosol generator just after termination of the inhalation cycle of the ventilator. Conveniently, the controller may be the same controller used to control the ventilator. In one aspect, the aerosol generator housing has a signal connector to which a control signal from the controller is inputted to control the operation of the aerosol generator. An interface may also be used to interface the aerosol generator with the controller. The interface may be mounted remote from the aerosol generator housing.

In another aspect, the liquid supplier is mounted to the aerosol generator housing. In this way, the liquid supplier and the aerosol generator are configured as a single unit. In a further aspect, the medication cup may be releasably mounted to the aerosol generator housing. As such, the medication cup may easily be removed when refilling and/or replacement is needed.

According to another embodiment of the invention, a connector is provided for delivery of medicament to the respiratory system. The connector comprises a generally T-shaped device having an inlet leg with a longitudinal axis and an outlet leg with an air inlet end and an aerosol outlet end. The inlet leg is connected to the outlet leg intermediate the air inlet end and the aerosol outlet end. The outlet leg has a first portion extending from the air inlet end to the connection to the inlet leg. The first portion has a longitudinal axis subtending at an angle of less than 90° with the longitudinal axis of the inlet leg.

In one aspect, the angle between the longitudinal axis of the first portion of the outlet leg and the longitudinal axis of the inlet leg is less than 80°. Ideally, the angle between the longitudinal axis of the first portion of the outlet leg and the longitudinal axis of the inlet leg is about 75°. The outlet leg may have a second portion extending from the first portion, with the second portion being substantially in line with the first portion.

In another embodiment, the invention provides a medication cup for receiving liquid medication for delivery to an aerosol generator. The medication cup has a reservoir for holding a medication and connector for connection to an aerosol generator. The medication cup has a releasable seal for maintaining the medication in the cup.

In one embodiment of the invention, the releasable seal comprises a sealing sheet releasably attached to the cup. Conveniently, a peel tab or other release mechanism may be used to remove the sheet. Alternatively the release mechanism may be a tab or other opener to perforate the sealing sheet when the cup is connected to the aerosol generator. The sheet may conveniently have an identifying code.

The invention further provides a nebulizer system for use with a ventilator circuit. The system comprises at least one tubing section having an inlet and an outlet for delivering air or other gases to a patient from a ventilator. The system further includes a nebulizer which delivers a nebulized fluid to the tubing section for inhalation by a patient on the ventilator. The nebulizer has a vibrating element having a front side, a back side and a plurality of openings. A fluid delivery system is employed to deliver fluid to the back side of the vibrating element. With this configuration, vibration of the vibrating element moves fluid from the back side of the vibrating element through the plurality of openings to produce the nebulized fluid which enters the tubing section for delivery to the patient.

In one aspect, the tubing section forms an air path and the source of fluid is separated from the air path by the vibrating element. In another aspect, the tubing section includes a T-shaped section. Conveniently, the source of fluid may include a capillary feed system which provides fluid to the back side of the vibrating element, and the vibrating element may comprise a ring-shaped piezoelectric element. The openings in the vibrating element may be sized to eject liquid droplets such that about 70% or more of the droplets by weight have a size in the range from about 1–5 micrometers.

In a further embodiment, a nebulizing device comprises a nebulizing element, and a fluid delivery system to deliver a fluid to the nebulizing element. At least one tube section is employed to define a delivery path to the patient. This delivery path is conveniently defined by a distance between the nebulizing element and the patient, and has a length of less than 500 mm, and preferably less than about 300 mm.

In one aspect, the nebulizing element has a vibrating element with openings therein. The vibrating element also has a front side and a back side, and the delivery path is defined at one end by the front side of the vibrating element. With this configuration, the fluid is delivered through the openings in the vibrating element upon vibration of the vibrating element, with the fluid being delivered to the back side of the vibrating element.

In another aspect, the tube section includes a T-shaped section having a top section and a central section, and the nebulizing element is positioned at a bottom of a central section. Ideally, the central section forms an angle of from 60° to 80° with a straight portion of the T-shaped section. In a further aspect, the tube section may include a Y-shaped section which separates into a first arm for inhalation and a second arm for exhalation. With this arrangement, the nebulizing element is coupled to a second tube section which is connected to the Y-section. Desirably, the second tube section is a T-shaped section which is attached to the Y-section. Preferably, the delivery path through the tube section is substantially free of baffles and flow disrupters.

The invention also provides a method of providing a nebulized fluid to a patient. According to the method, a vibratable member having a plurality of apertures that is in contact with a fluid is vibrated to produce a nebulized fluid. The nebulized fluid is permitted to eject into a conduit that is coupled to a ventilator. A gas from the ventilator is then employed to supply the aerosolized fluid to the patient's airway. Alternatively, the nebulized fluid may be provided to the patient using other techniques, such as by patient inhalation.

In one aspect, the distance between the vibratable member and the patient is less than about 500 mm, and in some cases less than about 300 mm. In this way, minimal tubing may be used to supply the aerosolized fluid to the patient, thereby requiring less energy to nebulize the fluid and reducing the generated heat so that the medication is not compromised.

The invention further provides a ventilator circuit that comprises a nebulizing element, and a fluid delivery system for delivering fluid to the nebulizing element. A ventilator is used to deliver and withdraw air from a patient. A control system is operably coupled to the nebulizing element and the ventilator. The control system is used to activate the nebulizing element during an inhalation cycle where respiratory gases are being supplied to the patient by the ventilator. For example, the controller may activate the nebulizing element within about 20 milliseconds of initiation of an inhalation cycle and deactivate the nebulizing element within 20 milliseconds of termination of the inhalation cycle. In this way, the aerosol is generated essentially only when gases are being supplied to the patient.

In one aspect, the nebulizing element has a vibrating element with openings therein, and a front side and a back side. The fluid is delivered through the openings in the vibrating element upon vibration of the vibrating element, and the fluid is provided to the back side of the vibrating element.

BRIEF DESCRIPTION OF THE DRAWINGS

The invention will be more clearly understood from the following description of some embodiments thereof, given by way of example only, with reference to the accompanying drawings, in which:

FIG. 3 is a perspective view of a connector piece of the apparatus of FIG. 1;

FIGS. 4(*a*) to 4(*d*) are elevational views of the apparatus of FIG. 1 in different orientations;

FIG. 12(*a*) is an exploded, perspective view of the liquid supplier of FIG. 9;

FIG. 14(*b*) is a front view of the apparatus of FIG. 14(*a*) in different orientations;

FIG. 17(*b*) is a side view of the apparatus of FIG. 1 in another configuration of use connected to a tracheal tube;

FIG. 17(*c*) is a perspective view from beneath of another medication cup of the apparatus of FIG. 1;

FIG. 21(*b*) is a perspective view along the rear side of the controller circuit of FIG. 21(*a*);

FIG. 21(*c*) is a perspective view of a mounting device according to the invention;

DESCRIPTION OF THE SPECIFIC EMBODIMENTS

Figure 1:
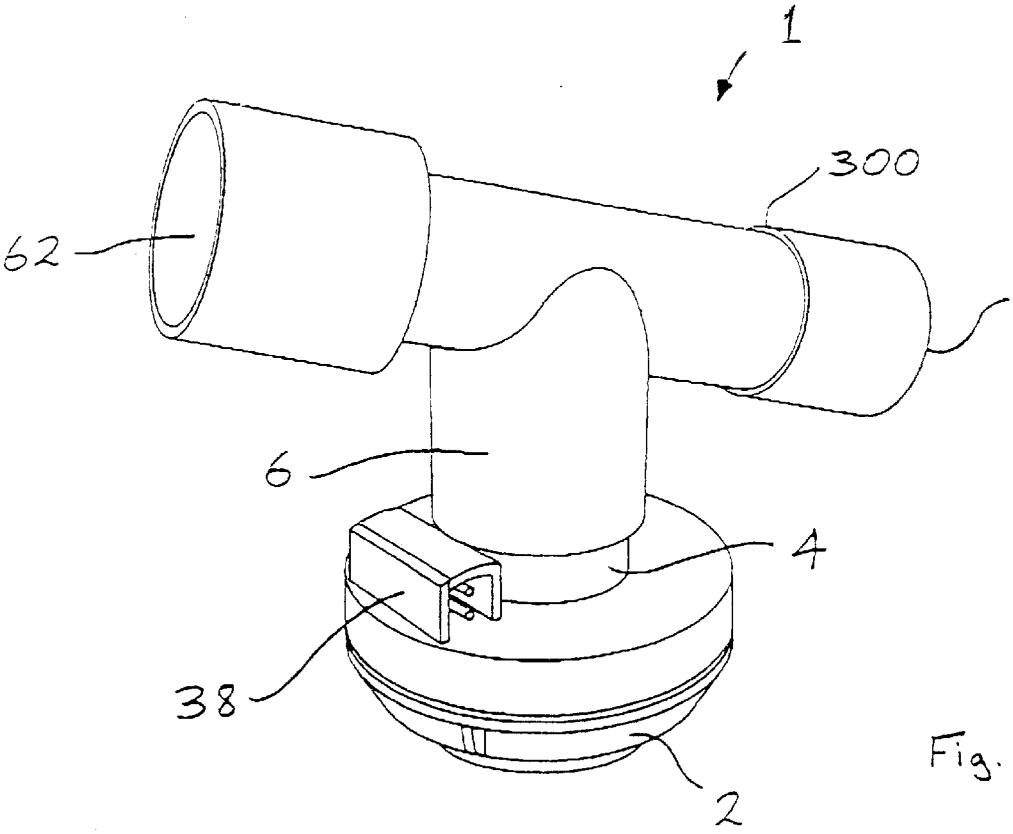
FIG. 1 is a perspective view of an apparatus for delivery of medicament to a respiratory system according to the invention.

Referring to the drawings and initially to FIG. 1 thereof, there is illustrated an apparatus 1 according to the invention for the delivery of medicament to the respiratory system of a patient. The apparatus 1 comprises a medication cup 2, an aerosol generator 3, a housing 4 for the aerosol generator 3, a liquid supplier 5 and a connector 6.

Liquid medication placed within the medication cup 2 is delivered up through the liquid supplier 5 by capillary action. An oscillatory motion of the liquid supplier 5 may also assist in pumping the liquid medication upwards. An aerosol of the medication is generated by the aerosol generator 3, the aerosol then passes through the aerosol generator housing 4 and into the connector 6. A gas, such as air or oxygen, enters the connector 6 through a gas inlet 61 of the connector 6 entraining the generated aerosol therein, and the air with entrained aerosol medication is delivered through an outlet 62.

Figure 2:
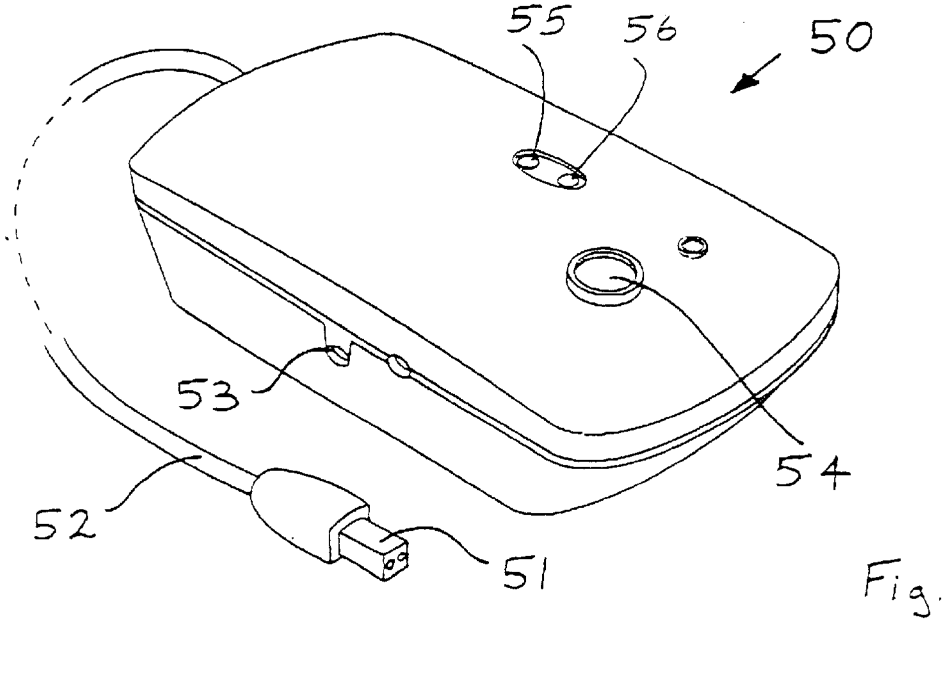
FIG. 2 is a perspective view of a controller.

A controller 50, which may be connected to the apparatus 1 by means of a control lead 52, controls the generation of the aerosol and the associated oscillation of the liquid supplier 5 (FIG. 2). The controller 50 has a power supply socket 53 and provides power to drive the generation of the aerosol as will be described in more detail below. In some embodiment, controller 50 may also be coupled to a ventilator.

Referring now to FIG. 3, the connector 6 has an aerosol inlet 60 for aerosol from the generator 3, a gas inlet 61 and an outlet 62 for aerosol and gas. The connector 6 is of a general T-shape, the longitudinal axis of the gas inlet 61 subtending an acute angle of 75° with the longitudinal axis of the aerosol inlet 60, as illustrated. The longitudinal axis of the gas inlet 61 is co-axial with the longitudinal axis of the outlet 62, and the connector 6 slightly tapers outwardly between the gas inlet 61 and the outlet 62.

The connector 6 is configured to entrain the aerosol generated by the aerosol generator 3, which passes from the aerosol generator housing 4 into the aerosol inlet 60, with a gas, such as air, which passes in through the gas inlet 61. The entrained medication aerosol/gas mixture passes out of the connector through the outlet 62.

The configuration of the connector 6 ensures the entrained aerosol/gas mixture passes out of the connector 6 through the outlet 62 regardless of the orientation of the connector 6, as illustrated in FIGS. 4(*a*) to 4(*d*). This is highly advantageous as it enables the user to operate the apparatus 1 in a wide variety of orientations, even with the longitudinal axis of the outlet 62 vertical, while being assured that the aerosol/gas mixture is always delivered through the outlet 62.

It will be appreciated that the angle between the longitudinal axis of the gas inlet 61 and the longitudinal axis of the aerosol inlet 60 may be any angle in the range of from 60° to 90°, but preferably less than 90°, and most preferably from 60° to 80°.

The gas inlet 61 may be connected to a ventilator 70 which pumps a gas, such as air into the connector 6. Alternatively, the apparatus 1 may be employed during manual breathing with the gas inlet 61 being open to atmosphere.

The medication cup 2, as illustrated in FIGS. 5 to 8, comprises a delivery tube 10 centrally located within the cup 2, and an annular reservoir 11 which surrounds the tube 10. Four inlet slots 13 are provided circumferentially spaced-apart around the wall of the tube 10 and a base 12 of the reservoir 11 slopes downwardly and inwardly to direct liquid medication to flow through the inlet slots 13 in the wall of the delivery tube 10 and into the tube 10. The delivery tube 10 extends below the level of the base 12 to form a central well 17. By spacing the inlet slots 13 around the circumference of the tube 10, this ensures that the liquid medicament will flow into the well 17 in a wide variety of orientations of the cup 2.

In this case, the tube 10 is integral with the cup 2. However, it will be appreciated that the tube 10 may alternatively be releasably attached to the cup 2.

A plurality of protuberances 14 are formed on the inner wall of the medication cup 2 to indicate the maximum volume of liquid medication to be inserted into the cup 2. In this case the maximum volume is about 10 ml, although other volumes may be used.

Figure 6:
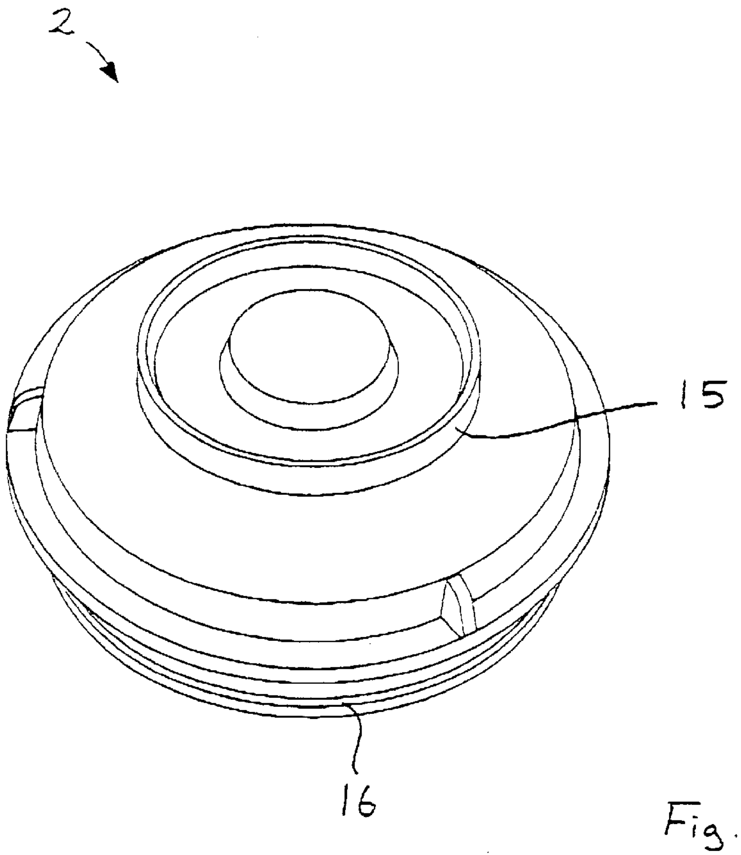
FIG. 6 is a perspective view from beneath of the medication cup of FIG. 5.

The medication cup 2 has an annular skirt 15, as illustrated in FIG. 6, formed on the base of the cup 2 to enable the cup 2 to be supported in an upright orientation. This allows a user to, for example, stand the cup 2 safely on a table before pouring liquid medication into the cup 2.

A screw thread 16 projects outwardly from the upright sides 18 of the cup 2 to enable releasable mounting of the medication cup 2 with the aerosol generator housing 4. The upright sides 18 have a chamfered edge 99 at the mouth of the cup 2.

Figure 7:
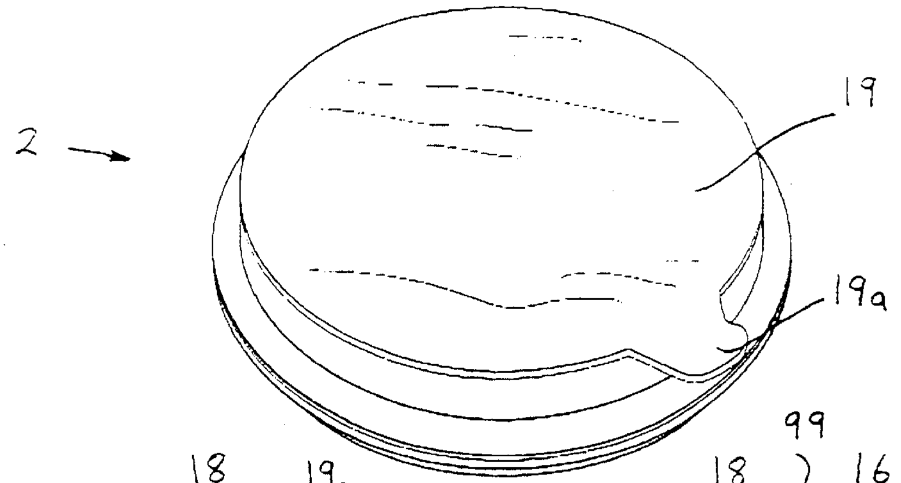
FIG. 7 is a perspective view from above of the medication cup of FIG. 5 after sealing.
Figure 8:
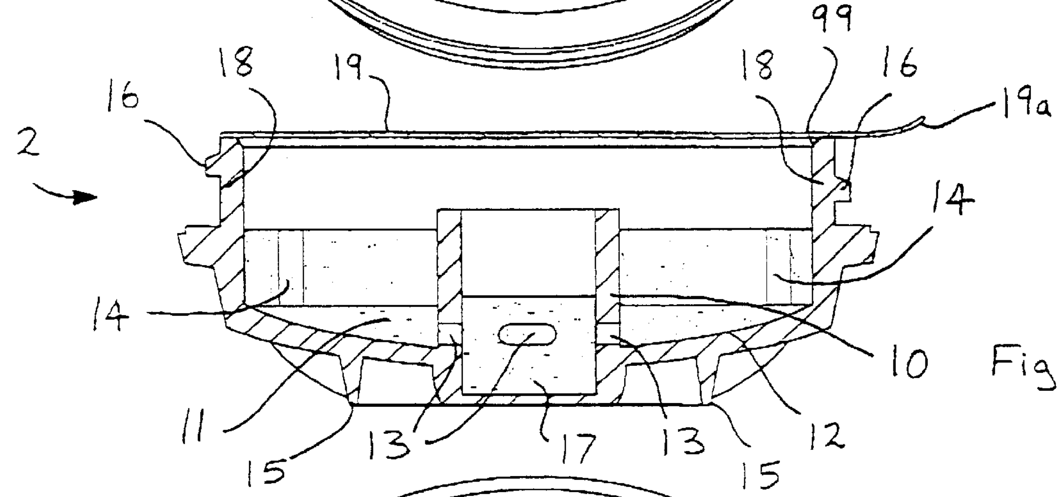
FIG. 8 is a side, cross-sectional view of the sealed medication cup of FIG. 7.
Figure 5:
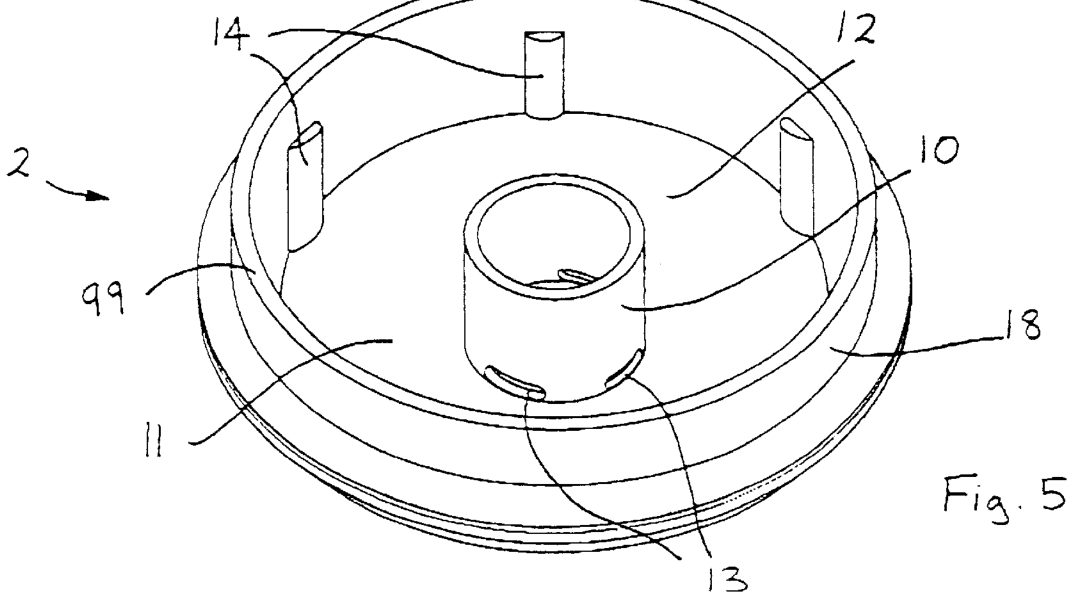
FIG. 5 is a perspective view from above of a medication cup of the apparatus of FIG. 1.

The medication cup 2 may be provided with a sealing sheet 19 to maintain the liquid medication in the cup 2 (FIGS. 7 and 8). The sheet 19 is releasably attached to the cup 2 and may be peeled off prior to use using a tab 19*a*. In this way medication may be preloaded into the cup 2 and stored in this way in a condition which is ready for use when required. It will be appreciated that the sealing sheet 19 may also be perforated by the downwardly protruding liquid supplier 5 during mating of the cup 2 with the housing 4 on assembly.

Information regarding, for example, the type of medication contained within the medication cup 2 or suitable dosages, or periods in which to use the medication may be provided on the sealing sheet 19. The information may be, for example, printed onto the sheet 19, or affixed with a label. The information may be, for example, in bar code format.

Figure 9:
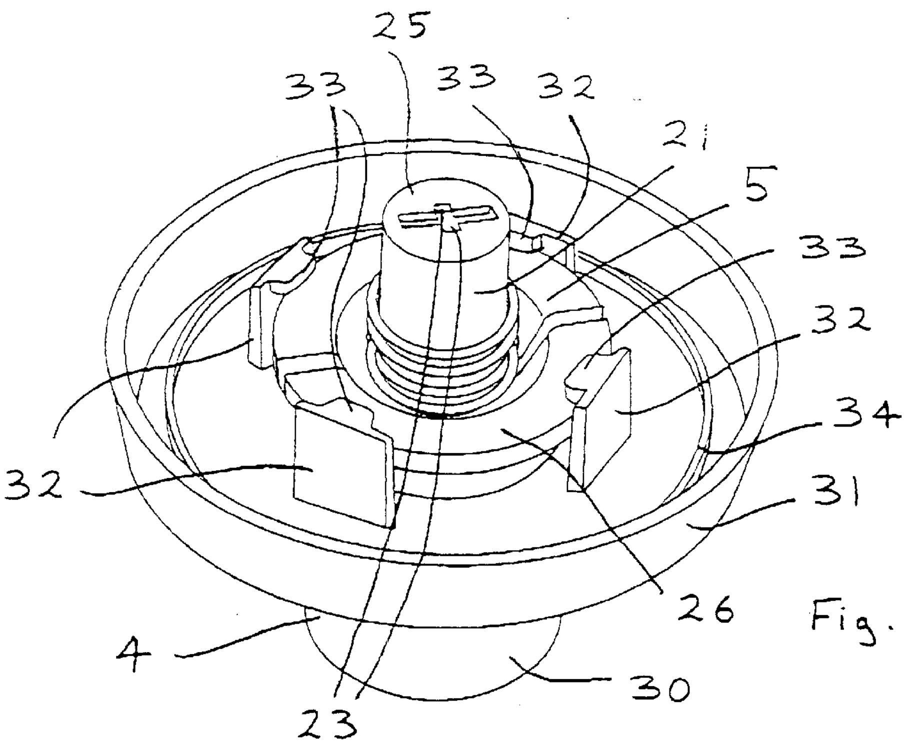
FIG. 9 is a perspective view from beneath of a liquid supplier of the apparatus of FIG. 1 mounted to an aerosol generator housing of the apparatus of FIG. 1.
Figure 10:
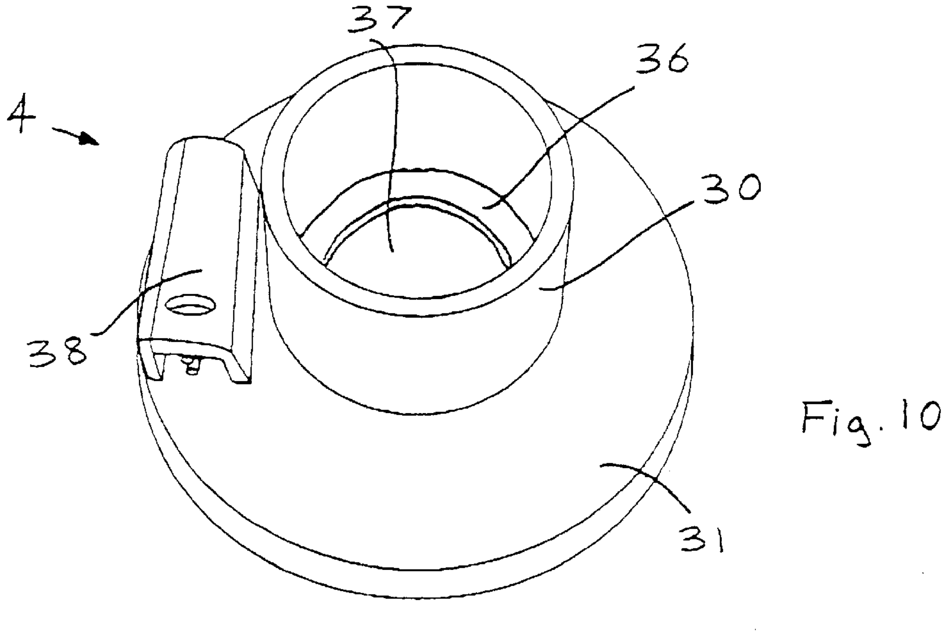
FIG. 10 is a perspective view from above of the aerosol generator housing of FIG. 9.

Referring now to FIGS. 9 to 12, the aerosol generator housing 4 comprises an iso-conical neck 30 extending from a shoulder part 31. The shoulder part 31 has four downwardly projecting and circumferentially spaced apart fingers 32, each finger 32 having a projection 33 on the lower end of the finger 32. In the assembled apparatus 1 the liquid supplier 5 is releasably held within the housing 4 by means of a snap-fit engagement between the projections 33 and the liquid supplier 5 (FIG. 9).

Figure 12:
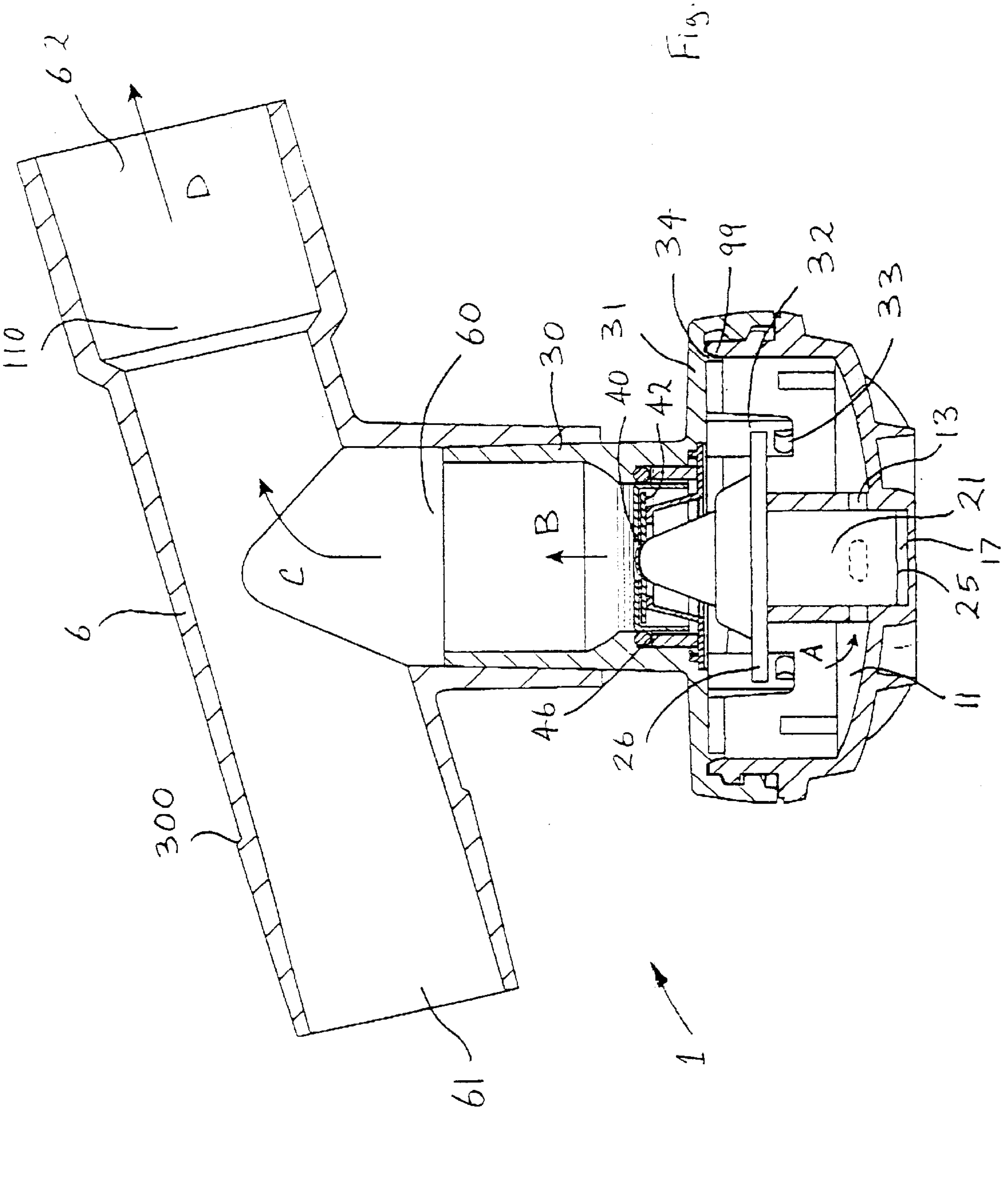
FIG. 12 is a side, cross-sectional view of the apparatus of FIG. 1 assembled.
Figure 12A:
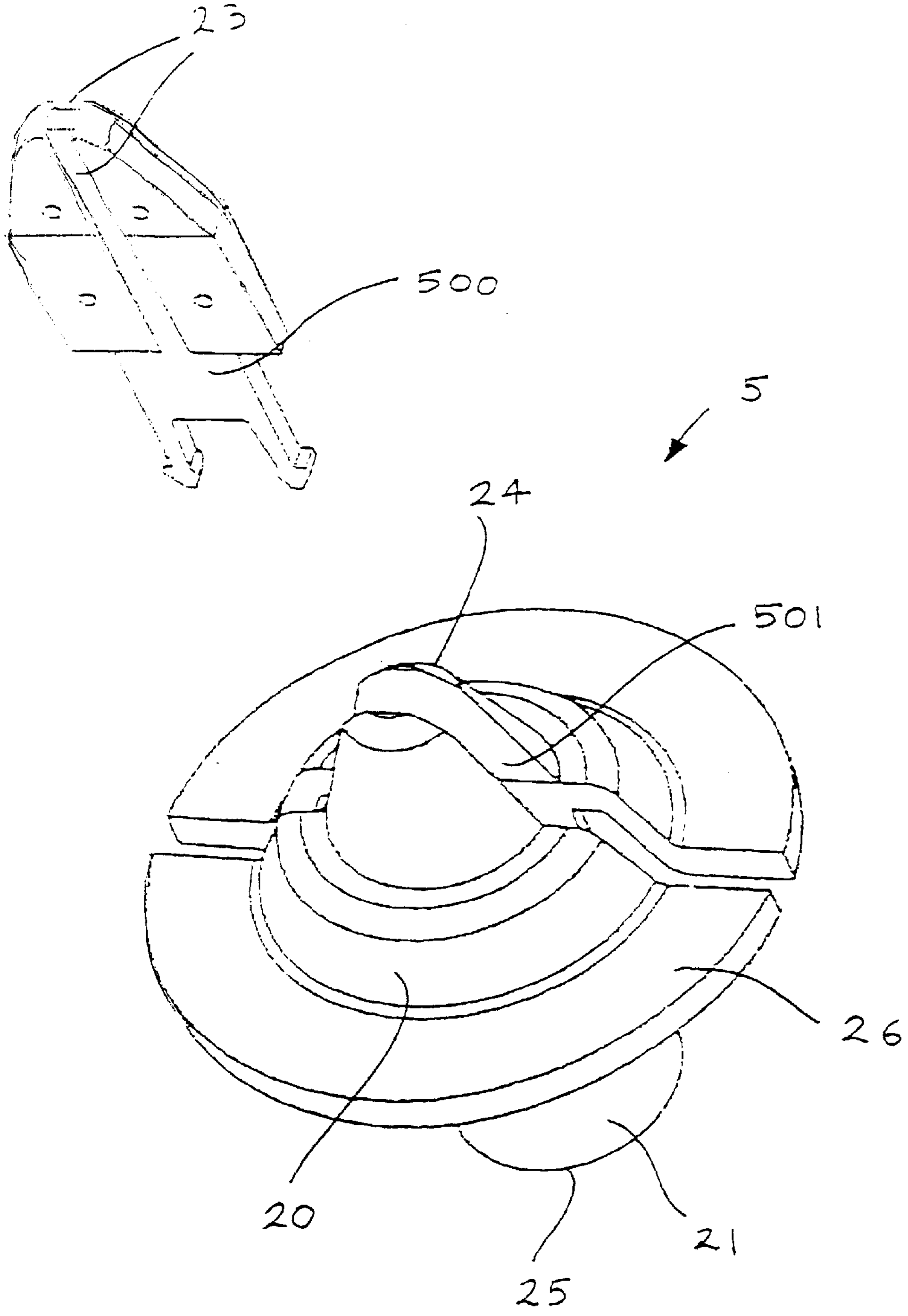

An annular sealing skirt 34 is formed on the shoulder part 31 extending downwardly. The skirt 34 is angled to sealingly engage the chamfered edge 99 of the mouth of the medication cup 2 in a wedge-seal arrangement, when the apparatus 1 is assembled (FIG. 12).

A screw thread 35 is formed on the inner sides of the shoulder part 31 to enable releasable mounting of the medication cup 2 to the aerosol generator housing 4. The neck 30 has an annular inward projection 36 formed above the shoulder part 31. The projection 36 defines a space 37 within the hollow neck 30, in which the aerosol generator 3 may be received.

The housing 4 also includes a connector port 38 rigidly attached to the upper surface of the shoulder part 31. Port 38 is configured to receive a docking member 51 of the control lead 52. A control signal from the controller circuit 50 is passed through the control lead 52 into the housing 4 via the port 38 to control the operation of the aerosol generator 3 and thus the generation of aerosol of medication.

The liquid supplier 5 comprises a head 20 and a stub 21 separated by an annular protruding flange 26. A coiled spring 22 is coaxially mounted around the stub 21. The outer diameter of the stub 21 is less than the inside diameter of the delivery tube 10, so that there is a clearance between the stub 21 and the tube 10 when the stub 21 is inserted into the tube 10 in the assembled apparatus 1(FIG. 12). The coiled spring 22 is at least partially compressed against the upper end of the delivery tube 10, and base 25 of the stub 21 extends below the slots 13 in the wall of the tube 10 and into the well 17 when assembled (FIG. 12).

The liquid supplier 5 includes two capillaries 23 which extend from the base 25 upwardly through the liquid supplier 5 to crown 24 of the head 20. The capillaries are open at the base 25 and at the crown 24 (FIG. 9). The capillaries 23 provide the flow path for the liquid medicament through the liquid supplier 5.

Illustrated in FIG. 12(*a*), the liquid supplier comprises an insert piece 500 which may be slidably received in a slot 501 in the head 20. Two elongate recesses in the insert piece 500 define the capillaries 23. In use each capillary 23 operates in a manner similar to a point of a fountain pen.

Figure 11:
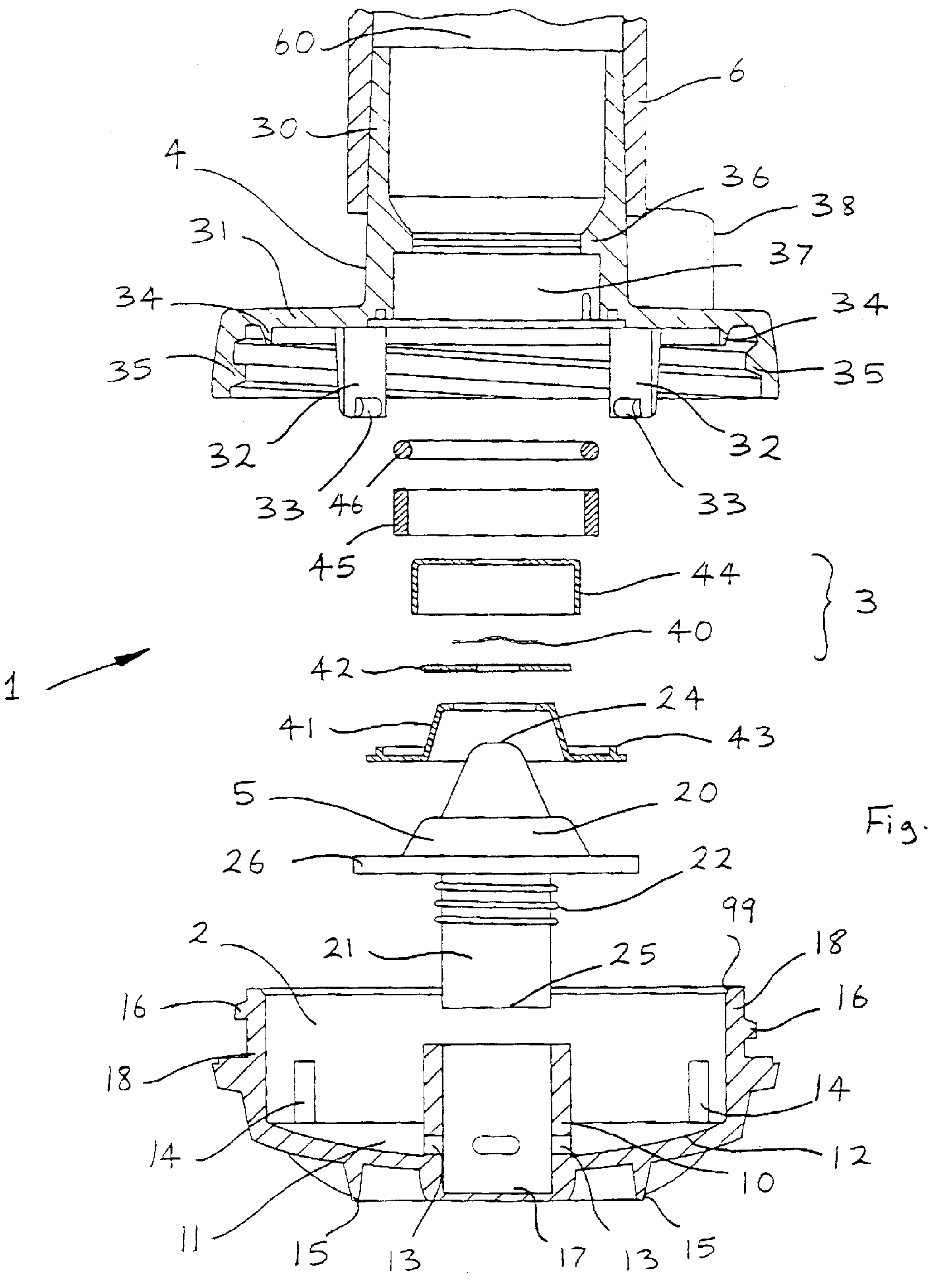
FIG. 11 is an exploded, side, cross-sectional view of the apparatus of FIG. 1.

The aerosol generator 3 comprises a non-planar member 40, which may be dome shaped in geometry, with a plurality of tapered apertures extending between a front surface and a rear surface thereof, as described in U.S. Pat. No. 5,164,740 (Ivri), U.S. Pat. No. 5,586,550 (Ivri et al), U.S. Pat. No. 5,758,637 (Ivri et al), and U.S. Pat. No. 6,085,740 (Ivri et al), the entire contents of which are incorporated herein by reference. The aerosol generator 3 further comprises a piezoelectric element 42 having a central opening and a housing 44 (FIG. 11). In the assembled apparatus 1, the non-planar member 40 and the piezoelectric element 42 are enclosed within the housing 44 in the neck space 37, and a shield 41 is fixedly attached to the shoulder part 31 by means of bonding a rim 43 to the housing 4 (FIGS. 11 and 12). The shield 41 has a central aperture for receiving the crown 27 of head 20, when assembled (FIG. 11).

The non-planar member 40 has a plurality of small holes through which small particles of medication pass and are ejected to form the aerosol of medication. An anti-bacterial coating may be applied to the member 40 to ensure a sterile aerosol flow of particles into neck 30.

The connector 6 may be releasably mounted to the housing 4 by means of a push-fit engagement between the aerosol inlet 60 and the neck 30 (FIG. 12).

To assemble the apparatus 1, the aerosol generator 3 is assembled and is inserted into the neck space 37 within a sleeve 45 between an O-ring seal 46 and the shield 41, which is bonded to the housing 4. The aerosol generator 3 has freedom to move between the O-ring 46 and the shield 41. The liquid supplier 5 is engaged with the housing 4 by means of the snap-fit of the projections 33 with the flange 26. Liquid medication is then poured into the reservoir 11 and the housing 4 is mated with the medication cup 2, the stub 21 being inserted into the delivery tube 10. The housing 4 and the cup 2 are rotated relative to one another to inter-engage the screw threads 35, 16 and thereby seal the housing 4 to the medication cup 2. Finally, the aerosol inlet 60 is pushed over the neck 30 to mount the connector 6 in a push-fit arrangement.

As illustrated in FIG. 12, the aerosol generator 3 is displaced from the liquid medicament in the medication cup 2. The liquid supplier 5 through capillary action and optionally in combination with an oscillatory pumping action delivers the liquid medicament to the aerosol generator 3.

In the assembled apparatus of FIG. 12, the crown 24 of the head 20 extends through the aligned apertures in the shield

41. Piezoelectric element 42 is connected to housing 44 to which the non-planar member 40 is coupled. In this case, the crown 24 extends through the apertures and contacts the non-planar member 40. In another embodiment of the invention, the crown 24 extends through the apertures towards the non-planar member 40 but terminates adjacent to the member 40 without contacting member 40.

In use and referring particularly to FIG. 12, the control lead 52 provides a power and a control signal to the piezoelectric element 42 to cause activation of the piezoelectric element 42, which in turn causes vibration of the non-planar member 40. In some embodiments, this vibration may act against the force of the coiled spring 22 to cause an oscillatory plunging motion of the liquid supplier 5. Liquid medication is thus delivered up through the capillaries 23 of the liquid supplier 5. Alternatively, the liquid medication may be drawn up through the capillaries 23 solely due to capillary action such that vibration of non-planar member 40 does not come into contact with head 20. Such a liquid delivery system may operate in a manner similar to that described in U.S. Pat. No. 5,938,117 and U.S. patent application Ser. No. 09/678,410, filed Oct. 2, 2000, the complete disclosures of which are herein incorporated by reference. The clearance between the delivery tube 10 and the stub 21 enables medication to flow from the reservoir 11 into the well 17 (flow A). During the motion of the liquid supplier 5, base 25 of the stub 21 always remains below the level of the slots 13 to ensure the liquid pressure in the capillaries 23 is not lost.

The droplets of liquid emerge from the capillaries 23 at the crown 24 where they contact the non-planar member 40, the vibration of which causes the liquid to pass through the holes in the member 40 and generates an aerosol of medication. The aerosol passes through the neck 30 (flow B) into the aerosol inlet 60 until it meets the flow of gas from the gas inlet 61. The aerosol is entrained with the gas (flow C) and passes out of the connector 6 through the outlet 62 (flow D).

Figure 13:
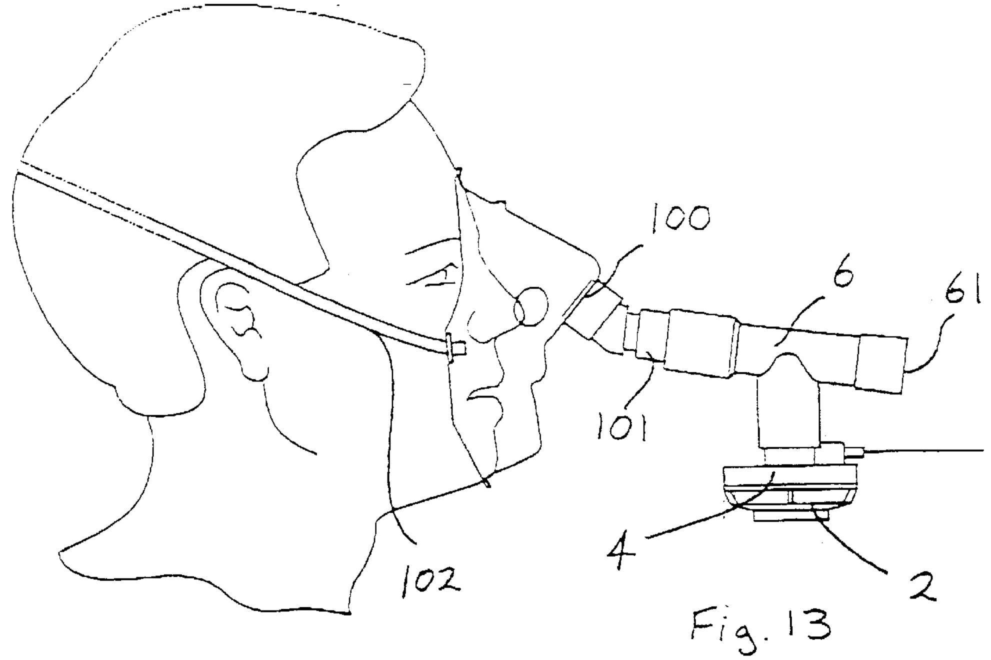
FIG. 13 is a side view of the apparatus of FIG. 1 in use connected to a face mask.
Figure 14A:
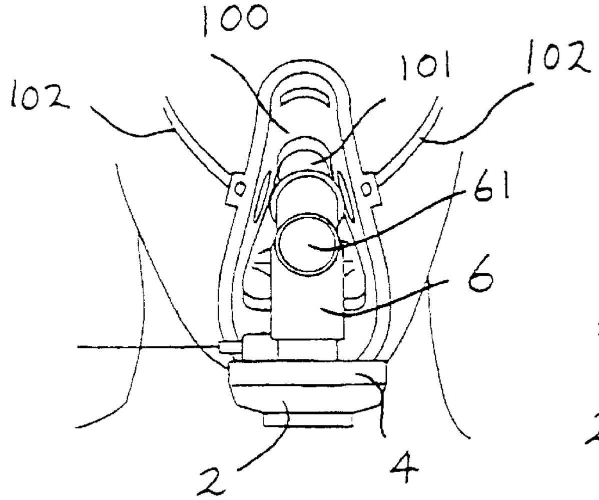
FIG. 14(*a*) is a front view of the apparatus and face mask of FIG. 13.
Figure 14B:
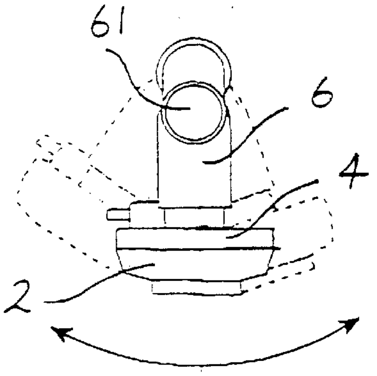

As illustrated in FIGS. 13 and 14, the outlet 62 of the connector 6 may be connected in communication with a face mask 100 to assist breathing of a patient. The connector 6 tapers outwardly in a step-wise manner to define a female connection recess 110 at the outlet 62 (FIG. 12). In this case, the face mask 100 is releasably mounted to the connector 6 by means of an interference fit between an inlet arm 101 to the face mask 100 and the recess 110.

The configuration of the T-shaped connector 6 means that an entrained mixture of aerosol medicament and gas is delivered from the connector outlet 62 through the inlet arm 101 to the face mask 100 and on to the respiratory system of the patient, in a wide variety of orientations of the apparatus 1, as illustrated in FIGS. 14(*a*) and 14(*b*). The apparatus 1 provides flexibility with regard to its possible uses, and is thus suitable for use with, for example, a reclining or sleeping patient.

The apparatus 1 is lightweight. By mounting the apparatus 1 to a face mask 100 which may be worn by a patient, the apparatus 1 may be used during movement of the patient. During such movement the apparatus 1 is supported by the face mask 100 due to the interference fit between the inlet arm 101 and the female connection recess 110, and the face mask 100 is in turn held in place on the patient by means of straps 102.

Figure 15:
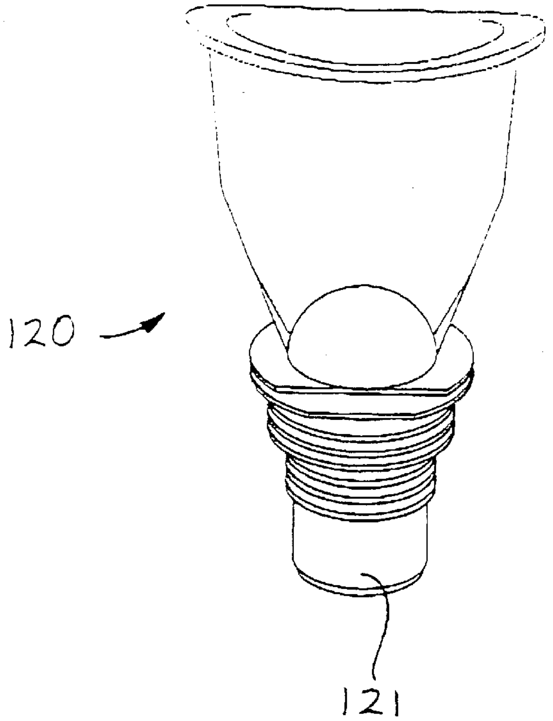
FIG. 15 is a perspective view of a mouthpiece.
Figure 16:
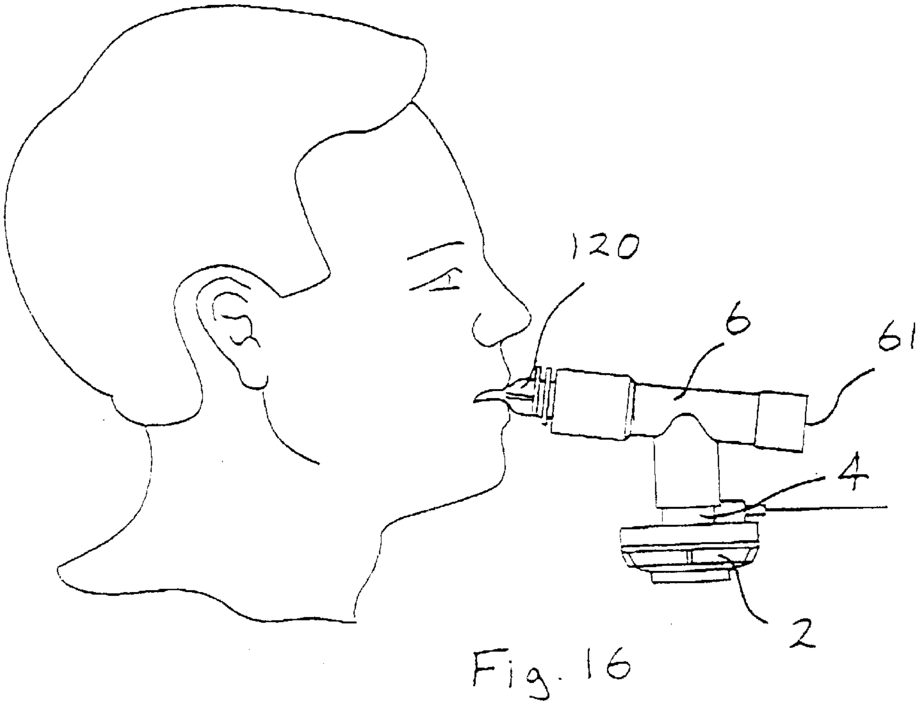
FIG. 16 is a side view of the apparatus of FIG. 1 in use connected to the mouthpiece of FIG. 15.

A breathing mouthpiece 120 may be used as an alternative to the face mask 100, as illustrated in FIGS. 15 and 16. The mouthpiece 120 is releasably mounted to the connector 6 by means of an interference fit between an inlet arm 121 to the mouthpiece 120 and the female connection recess 110 at the outlet 62.

Figure 17A:
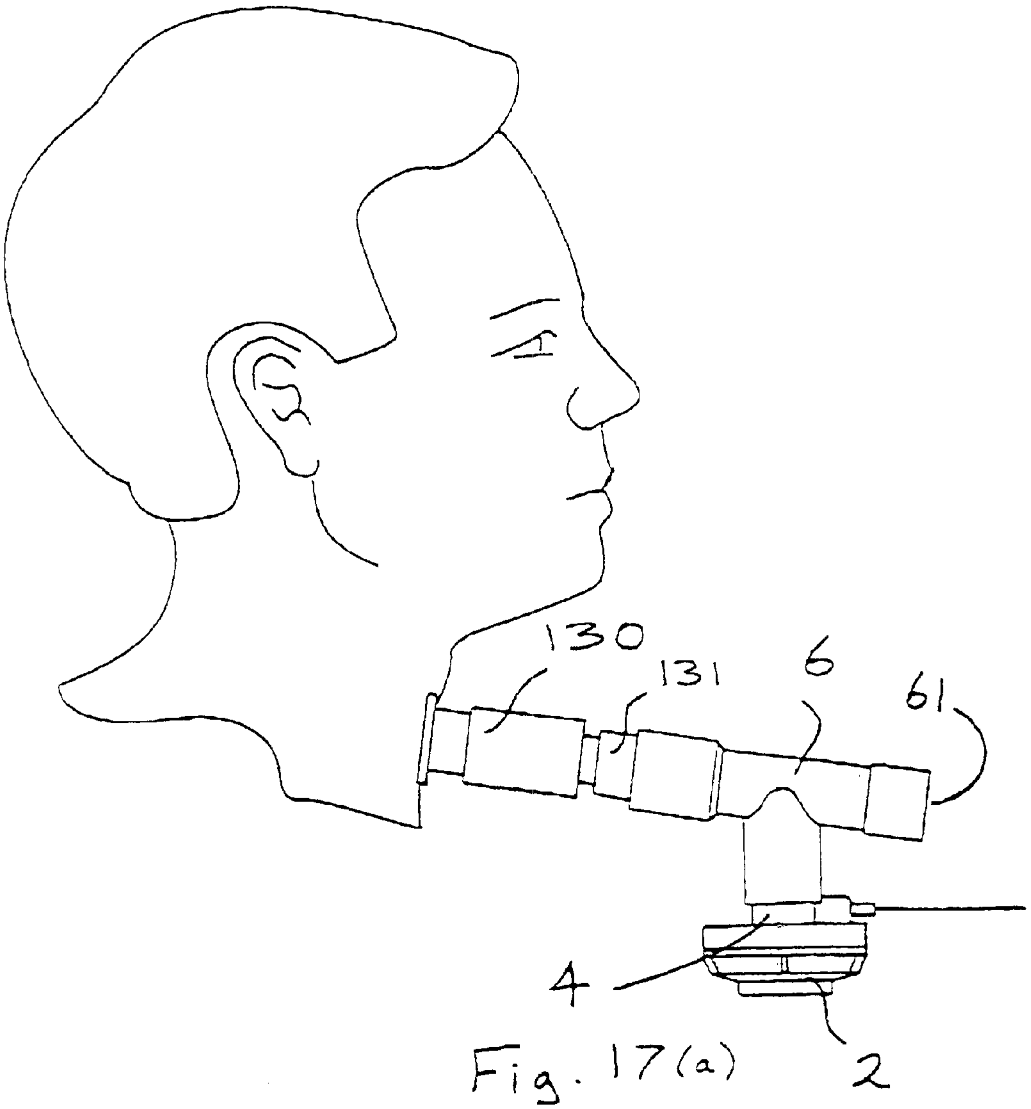
FIG. 17(*a*) is a side view of the apparatus of FIG. 1 in use connected to a tracheal tube.
Figure 17B:
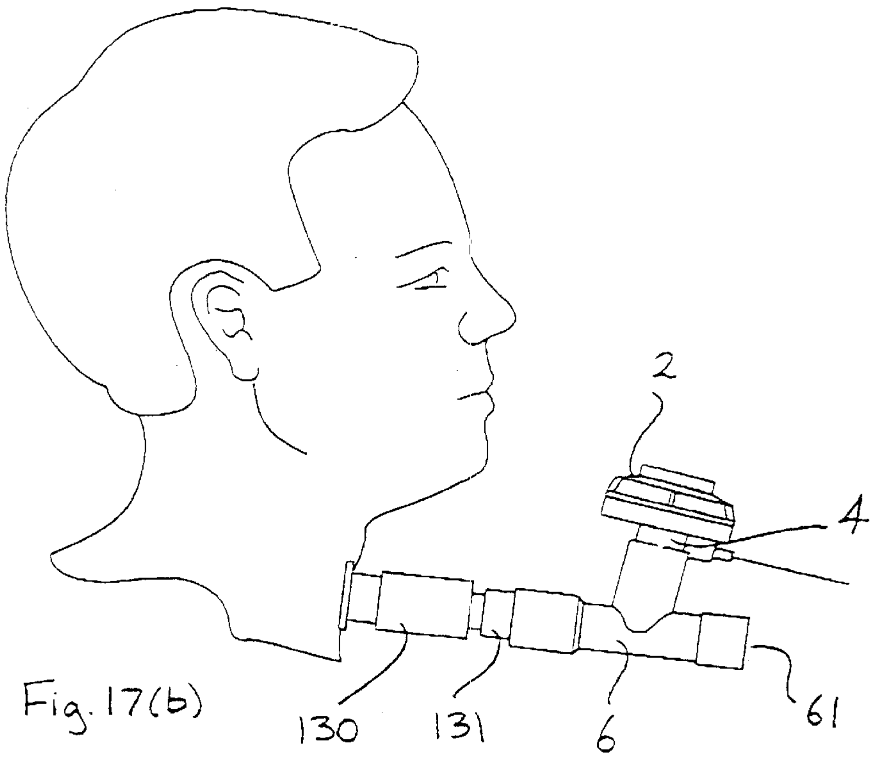
Figure 17C:
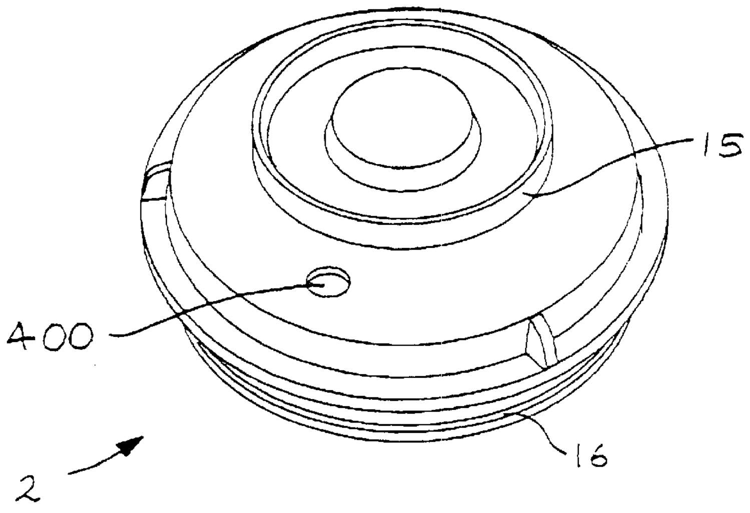

As a further alternative, a tracheal tube 130 may be used to assist breathing of a patient (FIG. 17(*a*)). The tracheal tube 130 is releasably mounted to the connector 6 by means of an interference fit between an inlet arm 131 to the tracheal tube 130 and the female connection recess 110 at the outlet 62.

The apparatus 1 delivers an entrained aerosol medicament and gas mixture out through the outlet 62 regardless of the orientation of the apparatus 1. As illustrated in FIG. 17(*b*), the apparatus 1 may be used in a configuration in which the medication cup 2 and the aerosol generator housing 4 are positioned above the connector 6. In this case, the liquid medicament is delivered through the liquid supplier 5 by gravitational action in addition to capillary action, and ins some cases pumping action also.

An insert aperture 400 may be provided in the base 12 of the medication cup 2, as illustrated in FIG. 17(*c*). The aperture 400 facilitates mating of an insert with the medication cup 2 in communication with the reservoir 11. The insert may contain a volume of liquid medicament and by mating the insert with the cup 2 via the aperture 400, the medicament can be delivered from the insert 400 directly to the reservoir 11 of the medication cup 2. This arrangement has the advantage that it is not necessary to disassemble the medication cup 2 from the aerosol generator housing 4 to refill the cup 2 after all of the medication has been delivered in an aerosol form to the respiratory system of the patient.

After delivery of medicament from the insert to the reservoir 11, the insert is normally removed and a plug is inserted into the aperture 400 to seal the reservoir 11.

A ventilator 200 may be connected to the gas inlet 61 of the connector 6 by means of an interference fit between a ventilator tube and the gas inlet 61. The connector 6 tapers outwardly near the gas inlet 61 to define a male connection protrusion 300 (FIG. 12) for a secure connection of the ventilator tube to the connector 6. The ventilator 200 may be used to pump air, or oxygen, or any other desired gas mixture into the connector 6 through the gas inlet 61 where it is entrained with aerosol medicament.

A Y-shaped connector piece may be provided in the ventilator tubing circuitry to provide one flow path for inhalation and an alternative flow path for exhalation. The Y-piece may be connected to the tubing circuitry either side of the apparatus 1.

Alternatively, the gas inlet 61 may be left open to atmosphere, in which case the patient breathes in through the connector 6 in the normal manner. In each case, the generated aerosol medicament is entrained with a gas, and the entrained mixture passes into the respiratory system of the patient through outlet 62.

The controller circuit 50 may be powered by an on-board power source, such as a rechargeable battery 201. Alternatively the controller circuit 50 may be connected to a remote power source by means of a power connection lead connected to the controller circuit 50 at power supply socket 53 (FIG. 2). The lead may be for connection to a mains power source 202, or alternatively to the ventilator 200 which provides the power for the controller circuit 50.

The controller circuit 50 preferably includes an on/off switch 54 to selectively control the operation of the aerosol generator 3, and two light emitting diodes (LED's) 55, 56. One LED 55 indicates the aerosol generator 3 is in an active state generating aerosol of medicament, and the other LED 56 indicates that the aerosol generator 3 is in a rest state. The switch 54 may alternatively be a reset switch.

Timing circuitry may further be provided as part of the controller circuit 50 to automatically switch between the active state of operation of the aerosol generator 3 and the rest state. The timing sequence may be programmable to activate generation of the aerosol a short period after commencement of an inhalation cycle, and to cease generation of the aerosol a short period after commencement of an exhalation cycle. In this way, phasic delivery may be precisely timed with aerosol generation.

Figure 18:
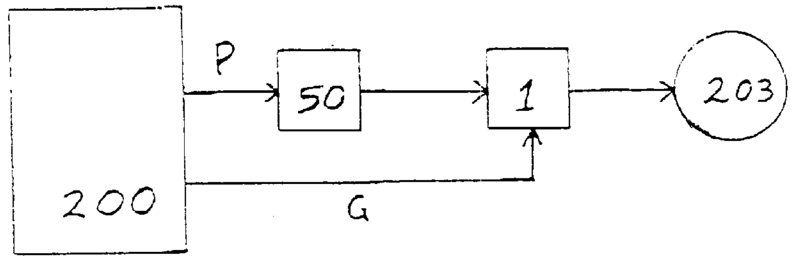
FIGS. 18 to 20 are flow diagrams illustrating operational arrangements for using the apparatus of FIG. 1.
Figure 19:
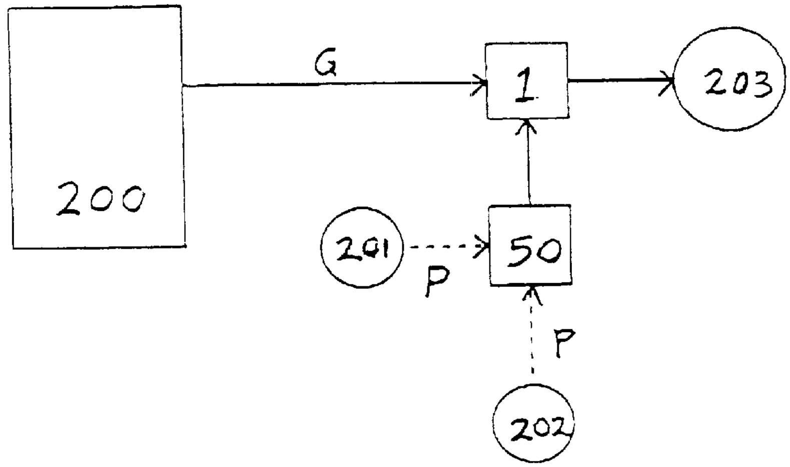
Figure 20:
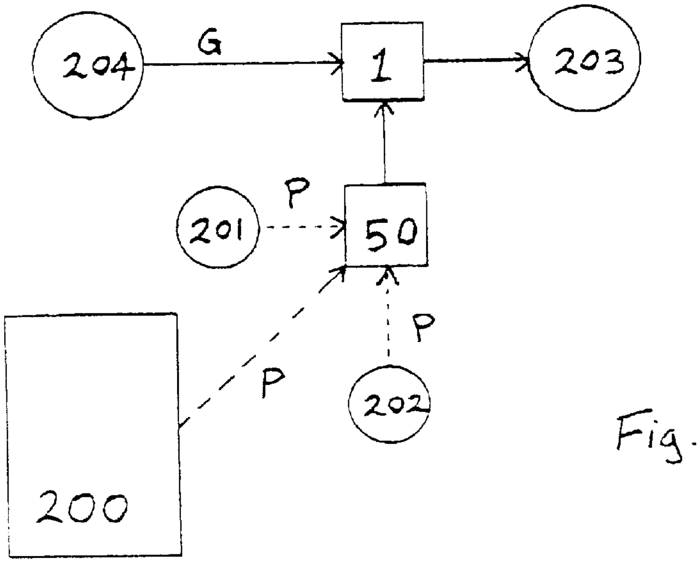

Referring now to FIGS. 18 to 20, there are illustrated some possible arrangements for using the apparatus 1, according to the invention, for delivering medicament to a respiratory system 203 of a patient.

In the arrangement of FIG. 18, gas is pumped from the ventilator 200 into the gas inlet 61 of the connector 6 (line G). The power source for the controller circuit 50 which controls operation of the apparatus 1 is provided by the ventilator 200 (line P).

In the arrangement of FIG. 19, gas is pumped from the ventilator 200 into the gas inlet 61 of the connector 6 (line G). The power source for the controller circuit 50 is provided by the battery 201 and/or the mains power source 202 (lines P).

In the arrangement of FIG. 20, gas is drawn into the connector 6 through the gas inlet 61 directly from the atmosphere 204 (line G). The power source for the controller circuit 50 is provided by the battery 201 and/or the mains power source 202 and/or the ventilator 200 (lines P).

In the case where the power source is provided by the battery 201, and the gas inlet 61 is open to the atmosphere 204, the apparatus 1 is highly mobile. In particular, the apparatus 1 may be worn or held by the patient as the patient takes exercise.

Figure 21B:
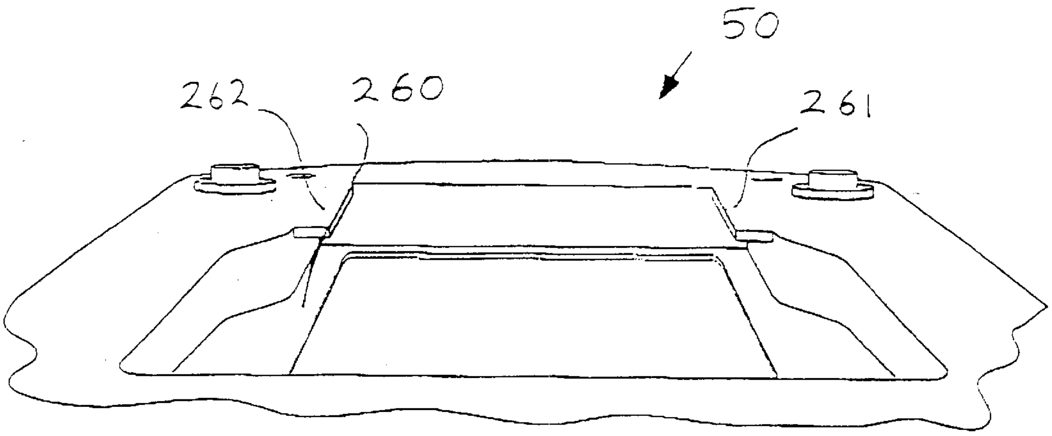
FIG. 21(*a*) is a plan view of a rear side of the controller circuit of FIG. 2.
Figure 21A:
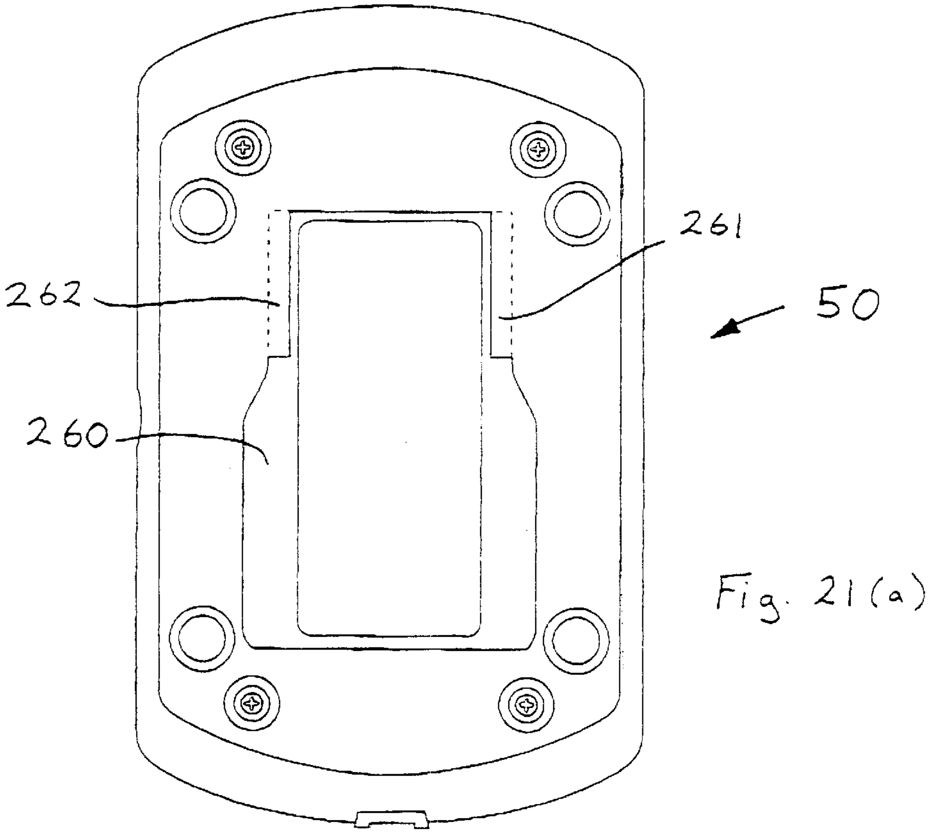
Figure 21C:
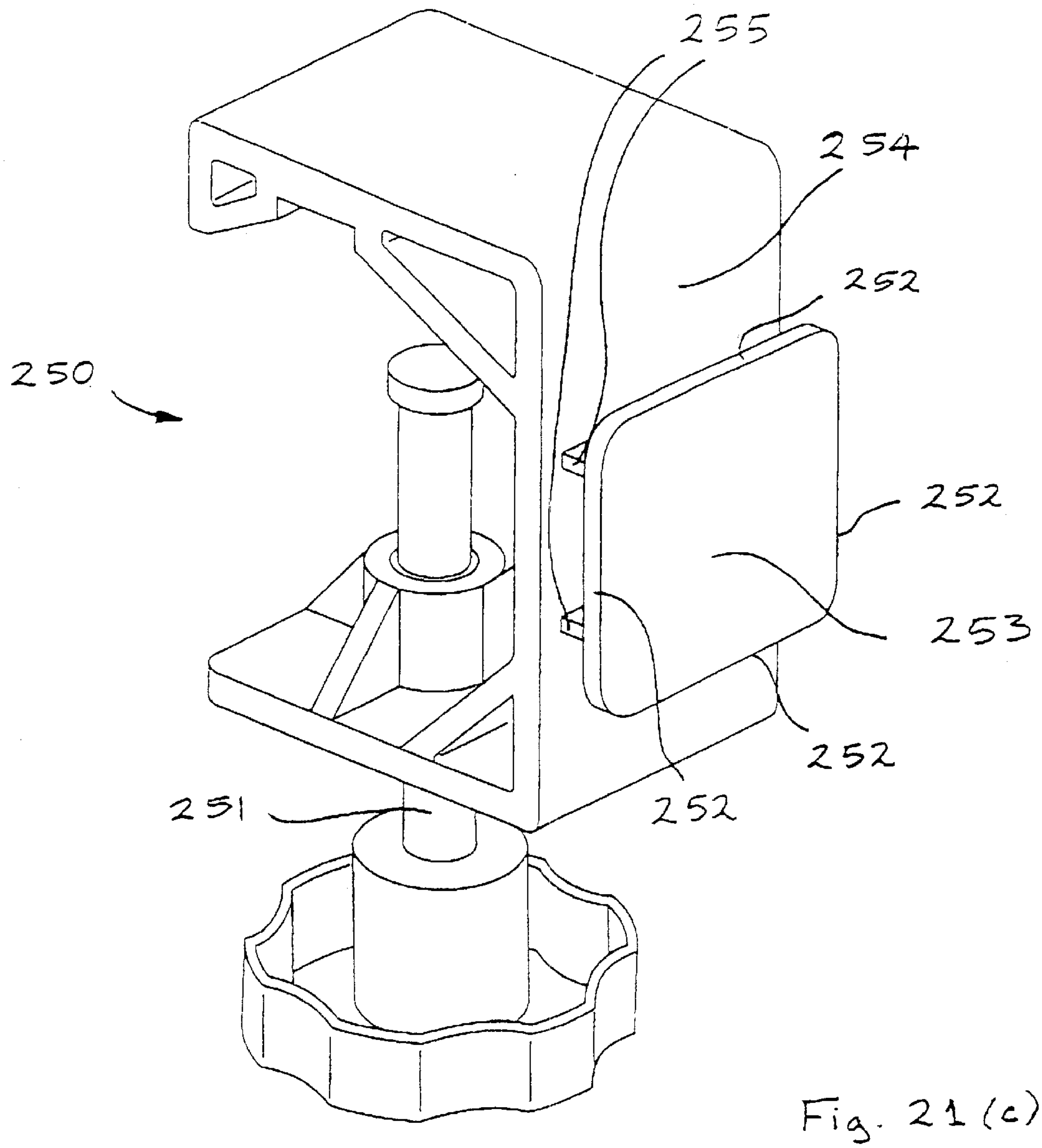

FIG. 21(*a*) illustrates a rear side of the controller circuit 50. The controller circuit 50 defines a recess 260 in the rear side of the controller circuit 50. The housing of the controller circuit 50 defies two ledges 261, 262 which overhang partially over recess 260, as illustrated most clearly in FIG. 21(*b*).

Referring now to FIG. 21(*c*), there is illustrated a mounting device 250. The mounting device 250 comprises means for attaching the device 250 to a support, such as an intravenous (IV) pole or a medi-rail, and hook means for supporting another medical device, in this case the controller circuit 50. The attachment means is provided, in this case, by a releasable clamp 251. The attachment means may alternatively be provided by a clip, such as a belt-clip.

The hook means is configured to define a plurality of, in this case four, support surfaces 252 for supporting the medical device in an upright configuration. The support surfaces 252 are provided by a lip 253 protruding from a main body 254 of the mounting device 250. The lip 253 is spaced from the main body 254 by two legs 255 (FIG. 21(*c*)).

Figure 22:
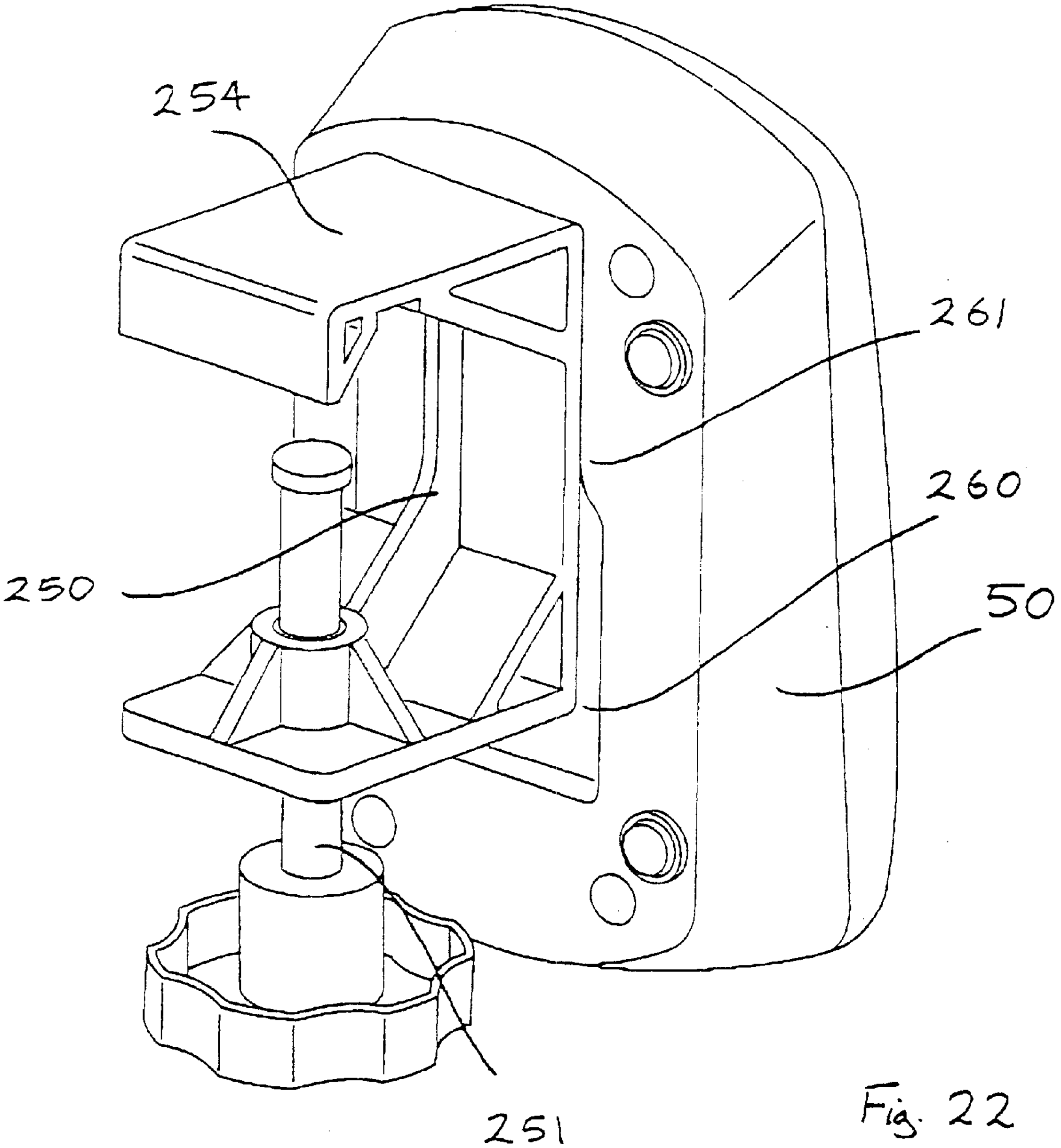
FIGS. 22 and 23 are perspective views of the mounting device of FIG. 21(*b*) in use with the controller circuit of FIG. 21(*a*)
Figure 23:
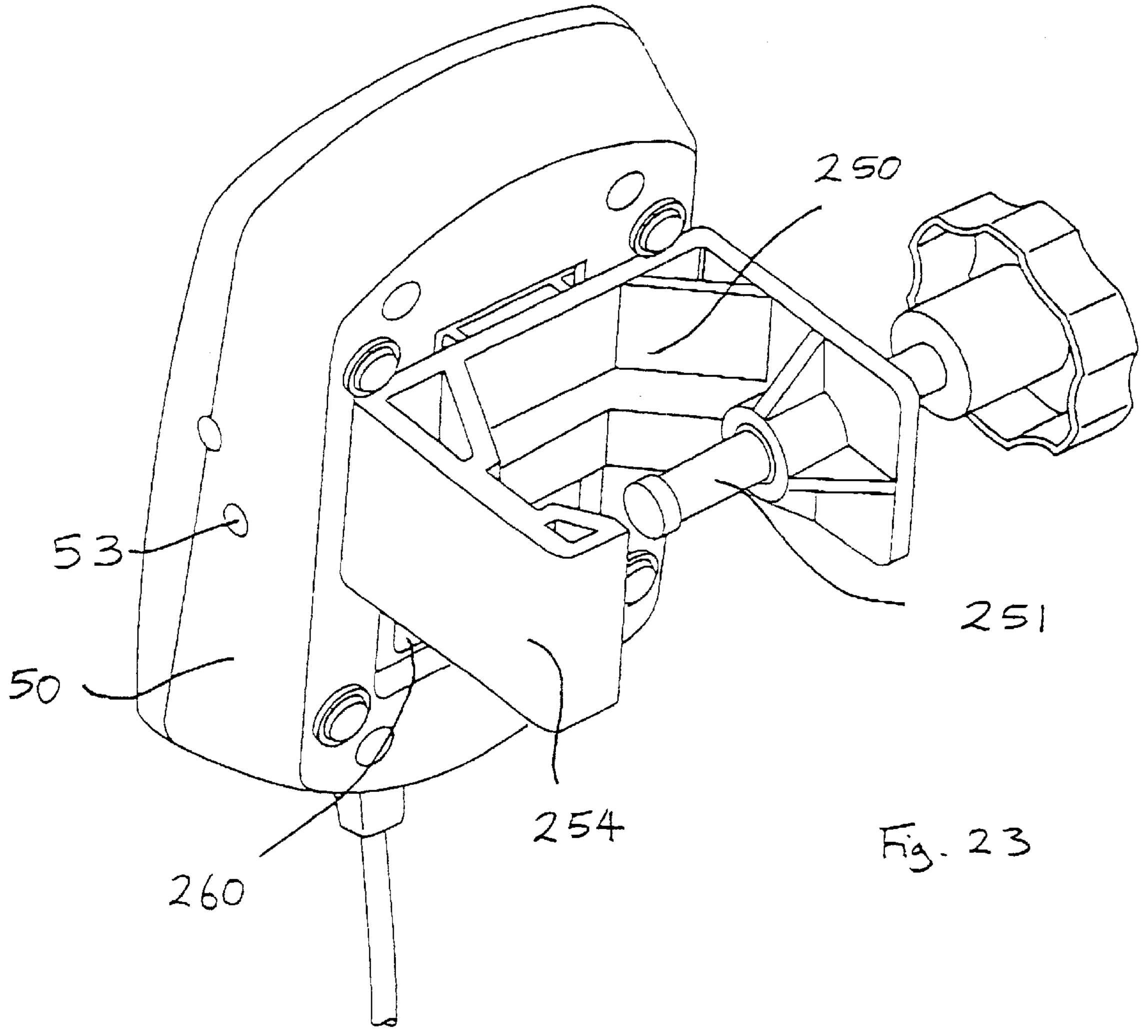

In this case, the mounting device 250 is used to support the controller circuit 50, as illustrated in FIGS. 22 and 23. The lip 253 of the mounting device 250 may be inserted into the wider end of the recess 260 in the rear side of the controller circuit 50 and then slid along the recess 260 until the lip 253 is partially enclosed behind the ledges 261, 262. In this configuration, the controller circuit 50 is releasably supported by the mounting device 250 (FIGS. 22 and 23).

The lip 253 comprises a plurality of support surfaces 252. This is advantageous, as it enables the controller circuit 50, or any other suitable medical device, to be supported in an upright orientation when the mounting device 250 is clamped to a horizontal support, such as a medi-rail (FIG. 22), or when the mounting device 250 is clamped to a vertical support, such as an IV pole (FIG. 23). It will be appreciated that the support surfaces 252 may be arranged at angles other than 90° relative to one another.

Figure 24:
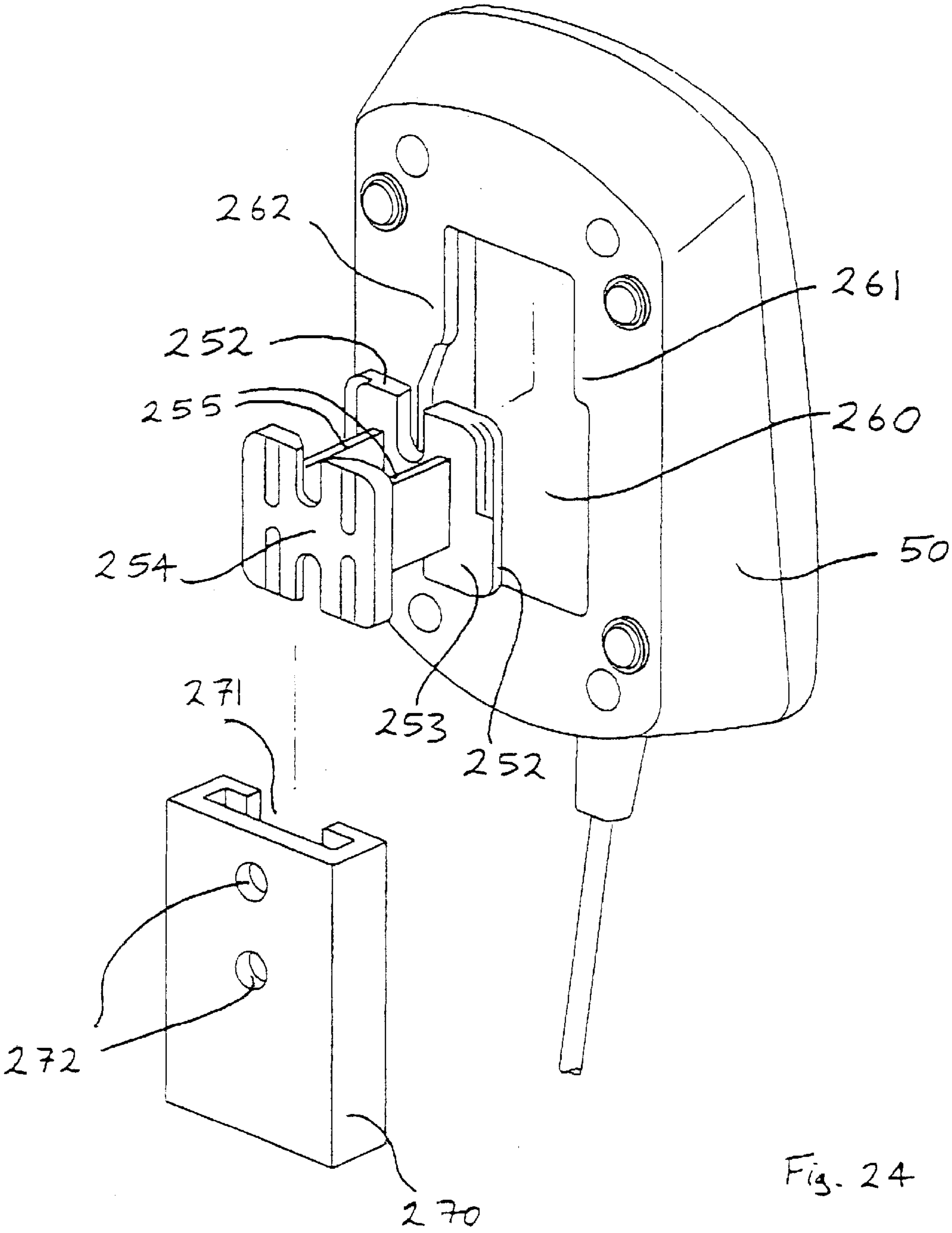
FIG. 24 is an exploded, perspective view of another mounting device according to the invention in use with the controller circuit of FIG. 21(*a*)
Figure 25:
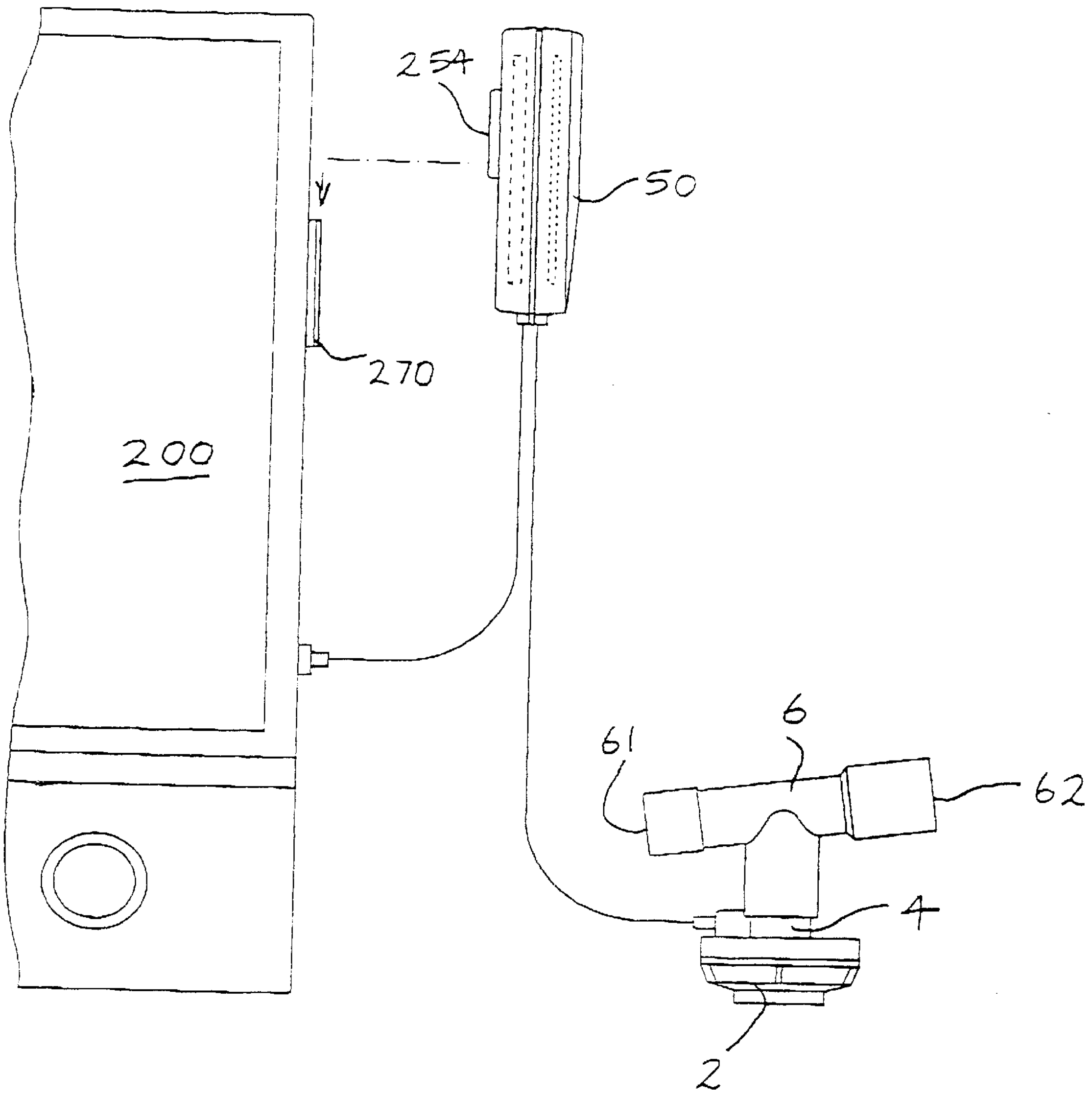
FIG. 25 is a side view of the apparatus of FIG. 1 in use with the controller circuit of FIG. 21(*a*) and the mounting device of FIG. 24.

Referring now to FIGS. 24 and 25 there is illustrated another mounting device which is similar to the mounting device 250 of FIGS. 21 to 23, and similar elements are assigned the same reference numerals in FIGS. 24 and 25.

In this case, the hook means may be moved relative to the attachment means to selectively disassociate the hook means from the attachment means, which is provided in this case by a sleeve 270. The sleeve 270 defines a groove 271 in which the main body 254 of the mounting device may be slidably received (FIG. 24).

The sleeve 270 may be permanently or temporarily attached to a support, such as a medi-rail, or an IV pole, or a ventilator 200, as illustrated in FIG. 25, by means of fixing pins inserted through apertures 272 in sleeve 270.

In one embodiment, the apparatus is provided as part of a ventilator circuit. In this case the ventilator circuit comprises a nebulizing element, a fluid source coupled to the nebulizing element for delivering fluid to the nebulizing element, and a ventilator which delivers and withdraws air from a patient. A control system is operably coupled to the nebulizing element and the ventilator. The control system activates the nebulizing element shortly before initiation of an inhalation cycle, for example within a time period such as 20 milliseconds and deactivates the nebulizing element shortly after termination of the inhalation cycle, for example within a time period such as 20 milliseconds. In this way, the aerosol is generated essentially only when the ventilator delivers a gas to the patient, thereby precisely controlling phasic delivery of a medication.

The apparatus will deliver medication in aerosol form to a patient in a wide variety of orientations of the apparatus. This is highly desirable as the apparatus may be directly attached to a patient breathing circuit and so reduce the length of tubing from the nebulizer to the mouth of the patient to less than 500 mm, usually less than 300 mm.

The apparatus provides a medication cup which is releasable from the aerosol generator housing. This is a highly efficient arrangement. When the liquid medicament has all been delivered to a patient respiratory system, the empty medication cup can be refilled with medicament, or can be replaced with a new cap full of medication in a quick and simple step. In this manner the apparatus may be reused many times.

The power usage of the apparatus is relatively low, in this case approximately 1.5W, thus the associated heat generated during use is negligible. The apparatus may be placed as close to the patient as desired, even touching the patient for long periods of use without causing discomfort to the patient, or without burning the patient.

The coiled spring is mounted to the liquid supplier, the medication cup is therefore free of all moving parts. The medication cup may simply be replaced as a refill container when the liquid medication has been used.

The liquid supplier, is held within the aerosol generator housing. Therefore, there are no loose parts which could be contaminated, broken or lost during refill of the medication cup, or replacement of the medication cup.

The aerosol generator produces an aerosol of medication within a controlled range of aerosol particle sizes. No degradation of the medication occurs as a result of the aerosol generation process.

The invention is not limited to the embodiments hereinbefore described which may be varied in construction and detail.

What is claimed is:

1. An apparatus for delivery of a medicament to the respiratory system, the apparatus comprising:

a reservoir adapted to hold a liquid medicament that is to be delivered to a respiratory system;

an aerosol generator that is adapted to aerosolize the liquid medicament;

a liquid supplier adapted to deliver the liquid medicament from the reservoir to the aerosol generator, wherein the liquid supplier is releasably mounted to a housing of the aerosol generator with a plurality of fingers for snap-fit engagement; and a connector to which the aerosol generator is operably connected, wherein the connector comprises a gas conduit having an inlet, an outlet, and an aerosol supply conduit, wherein the aerosol generator is configured to provide the aerosolized liquid medicament into the gas conduit through the aerosol supply conduit, and wherein the gas conduit is adapted to pass gases to entrain the aerosolized liquid medicament.

2. Apparatus as claimed in claim 1, wherein the aerosol supply conduit subtends an angle less than 90° with the inlet side of the gas conduit.

3. Apparatus as claimed in claim 2, wherein the aerosol supply conduit subtends an angle of less than 80° with the inlet side of the gas conduit.

4. Apparatus as claimed in claim 3, wherein the aerosol supply conduit subtends an angle of about 75° with the inlet side of the gas conduit.

5. Apparatus as claimed in claim 1, wherein the connector is mounted to the aerosol generator housing at the aerosol supply conduit.

6. Apparatus as claimed in claim 1, wherein the outlet of the gas conduit at least partially tapers outwardly.

7. Apparatus as claimed in claim 1, wherein the gas conduit comprises an outlet connector that is adapted to connect the gas conduit to a respiratory system.

8. Apparatus as claimed in claim 7, wherein the outlet of the gas conduit tapers outwardly in a step-wise manner to define a female connection recess at the outlet.

9. Apparatus as claimed in claim 7, further comprising a respiratory conduit that is adapted to connect the outlet of the gas conduit to a respiratory system.

10. Apparatus as claimed in claim 9, wherein the respiratory conduit is mounted to the connector at the outlet of the gas conduit.

11. Apparatus as claimed in claim 10, wherein the respiratory conduit is releasably mounted to the connector at the outlet of the gas conduit.

12. Apparatus as claimed in claim 10, wherein the respiratory conduit is mounted to the connector by an interference fit between the respiratory conduit and the outlet of the gas conduit.

13. Apparatus as claimed in claim 9, wherein the respiratory conduit is selected from a group consisting of a mouthpiece, a face mask, and an intertracheal tube.

14. Apparatus as claimed in claim 1, wherein the gas conduit comprises an inlet connector that is adapted to connect the connector to a ventilator.

15. Apparatus as claimed in claim 14, wherein the gas conduit comprises a male protrusion, and the inlet connector is at least partially provided by the protrusion.

16. Apparatus as claimed in claim 14, wherein further comprising a ventilator conduit to connect the gas conduit to a ventilator.

17. Apparatus as claimed in claim 16, wherein the ventilator conduit is mounted to the inlet connector of the gas conduit.

18. Apparatus as claimed in claim 17, wherein the ventilator conduit is releasably mounted to the inlet connector of the gas conduit.

19. Apparatus as claimed in claim 17, wherein the ventilator conduit is mounted to the inlet connector by an interference fit between the ventilator conduit and the gas conduit.

20. Apparatus as claimed in claim 1, wherein the aerosol generator comprises a vibratable member having a plurality of apertures extending between a first surface and a second surface thereof.

21. Apparatus as claimed in claim 20, wherein the first surface is adapted to receive the liquid medicament from the liquid supplier.

22. Apparatus as claimed in claim 20, wherein the aerosol generator is configured to generate the aerosol at the second surface of the vibratable member.

23. Apparatus as claimed in claim 20, wherein the vibratable member is dome shaped in geometry.

24. Apparatus as claimed in claim 20, wherein the vibratable member comprises a piezoelectric element.

25. Apparatus for delivery of medicament to a respiratory system comprising:

a medication cup that is adapted to receive a liquid medicament to be delivered to a respiratory system;

an aerosol generator;

a housing in which the aerosol generator is disposed, wherein the housing is releasably coupled to the medication cup;

a liquid supplier that is adapted to deliver the liquid medicament from the cup to the aerosol generator, wherein the liquid supplier is releasably mounted to the aerosol generator housing with a plurality of fingers for snap-fit engagement; and a connector that is adapted to receive aerosol generated by the aerosol generator is delivered.

26. Apparatus as claimed in claim 25, wherein the aerosol generator is displaced from the medication cup, and wherein the liquid supplier is adapted to deliver the liquid medicament between the cup and the aerosol generator.

27. Apparatus as claimed in claim 25, wherein the plurality of fingers are circumferentially spaced apart.

28. Apparatus as claimed in claim 25 wherein the aerosol generator housing comprises four fingers.

29. Apparatus as claimed in claim 25, wherein the liquid supplier defines an annular protruding neck.

30. Apparatus as claimed in claim 25, wherein the medication cup is sealingly mounted to the aerosol generator housing.

31. Apparatus as claimed in claim 30, wherein the aerosol generator housing comprises a skirt extending to sealingly engage the medication cup.

32. Apparatus as claimed in claim 31, wherein the skirt has an angled surface to sealingly engage a chamfered mouth of the medication cup.

33. Apparatus as claimed in claim 25, wherein the medication cup is releasably mounted to the aerosol generator housing by a screw-thread engagement.

34. Apparatus as claimed in claim 25, wherein the medication cup defines a reservoir for the liquid medicament, and further comprising a medication delivery tube extending from the reservoir, the liquid supplier being at least partially received within the delivery tube for delivery of the liquid medicament to the aerosol generator.

35. Apparatus as claimed in claim 34, wherein the delivery tube is provided by the medication cup.

36. Apparatus as claimed in claim 35, wherein the delivery tube is integral with the medication cup.

37. Apparatus as claimed in claim 35, wherein the delivery tube is attached to the medication cup.

38. Apparatus as claimed in claim 34, wherein the delivery tube has an inlet that is adapted to receive the liquid medicament from the reservoir.

39. Apparatus as claimed in claim 38, wherein the inlet includes a number of inlet slots which are circumferentially spaced-apart around the delivery tube.

40. Apparatus as claimed in claim 38, wherein a base of the reservoir at least partially slopes downwards towards the delivery tube.

41. Apparatus as claimed in claim 38, wherein at least part of the liquid supplier extends below the inlet.

42. Apparatus as claimed in claims 34, wherein the reservoir includes a refill port.

43. Apparatus as claimed in claim 42, wherein the refill port is provided in a base of the reservoir.

44. Apparatus as claimed in claim 43, further comprising a plug to selectively seal the refill port.

45. Apparatus as claimed in claim 34, wherein the reservoir comprises a central well from which the delivery tube extends.

46. Apparatus as claimed in claim 34, wherein the liquid supplier comprises a resilient member to reciprocate the liquid supplier in the delivery tube.

47. Apparatus as claimed in claim 46, wherein the resilient member is engagable with a free end of the delivery tube.

48. Apparatus as claimed in claim 46, wherein the resilient member comprises a spring.

49. Apparatus as claimed in claim 34, wherein the medication cup comprises at least one depth indicator to indicate the volume of liquid medicament in the reservoir.

50. Apparatus as claimed in claim 49, wherein the depth indicator comprises an internal marking on a wall of the medication cup.

51. Apparatus as claimed in claim 25, wherein the medication cup has a base that is adapted to hold the cup in an upright orientation when receiving the liquid medicament.

52. Apparatus as claimed in claim 51, wherein the base includes a support skirt extending from the base of the medication cup.

53. Apparatus for delivery of medicament to a respiratory system comprising:

a reservoir that is adapted to hold a liquid medicament to be delivered to a respiratory system;

an aerosol generator;

a housing for the aerosol generator;

a liquid supplier that is adapted to deliver the liquid medicament from the reservoir to the aerosol generator, wherein the liquid supplier is releasably mounted to the aerosol generator housing with a plurality of fingers for snap-fit engagement; and a connector through which aerosol generated by the aerosol generator is delivered;

wherein the aerosol generator housing includes a signal interface that is configured to receive control signals to control the operation of the aerosol generator.

54. Apparatus as claimed in claim 53, further comprising a controller to control the operation of the aerosol generator, the controller being connectable to the signal interface.

55. Apparatus as claimed in claim 54, wherein the controller comprises control means having an on-board power source.

56. Apparatus as claimed in claim 55, wherein the power source is a battery.

57. Apparatus as claimed in claim 56, wherein the battery is rechargeable.

58. Apparatus as claimed in claim 54, wherein the controller includes a power connector, the power connector being connectable to a remote power source.

59. Apparatus as claimed in claim 58, wherein the power connector comprises a ventilator power connection lead for connection to a ventilator power source.

60. Apparatus as claimed in claim 59 wherein the power connection lead is detachable from a socket in the control means.

61. Apparatus as claimed in claim 58, wherein the power connector comprises a main power connection lead for connection to a main power source.

62. Apparatus as claimed in any 54, wherein the controller comprises a timer to automatically switch the aerosol generator between an active state and a rest state.

63. Apparatus as claimed in claim 62, wherein the timer is selectively programmable.

64. Apparatus as claimed in claim 54, wherein the controller comprises user interface to selectively control the operation of the aerosol generator.

65. Apparatus as claimed in claim 64, wherein the user interface is remote from the aerosol generator housing.

66. Apparatus as claimed in claim 65, wherein the user interface means comprises a reset switch.

67. Apparatus as claimed in claim 64, wherein the user interface comprises an on/off switch.

68. Apparatus as claimed in claims 54, wherein the controller comprises status indication means to indicate the operational state of the aerosol generator.

69. Apparatus as claimed in claim 68, wherein the status indication means comprises at least one visual indicator.

70. Apparatus as claimed in claim 69, wherein the status indication means comprises two light emitting diodes, one to indicate an active state of operation of the aerosol generator, and the other to indicate a rest state of the aerosol generator.

71. Apparatus as claimed in claim 54, wherein the controller comprises a housing having a support to receive a mounting device.

72. Apparatus as claimed in claim 71, wherein the support comprises a recess in the housing for receiving a mounting device.

73. Apparatus as claimed in claim 72, wherein the support comprises at least one ledge overhanging the recess for engagement of a mounting device in the recess.

74. Apparatus as claimed in claim 73, wherein the support comprises two ledges on opposite sides of the recess.

75. Apparatus as claimed in claim 71, further comprising a mounting device to support the controller.

76. Apparatus as claimed in claim 75, wherein the mounting device comprises means for attaching the mounting device to a support; and hook means for supporting the control housing, the hook means being configured to define a plurality of support surfaces for supporting the control housing in an upright configuration.

77. Apparatus as claimed in claim 76, wherein the support surfaces each comprise a lip protruding from a main body of the mounting device.

78. Apparatus as claimed in claim 77, wherein the lip is engagable in the recess in the housing to support the control means.

79. Apparatus as claimed in claim 76, wherein the hook means defines four support surfaces.

80. Apparatus as claimed in claim 79, wherein each support surface is substantially perpendicular to an adjacent support surface.

81. Apparatus as claimed in claim 76, wherein the attachment means is releasable.

82. Apparatus as claimed in claim 76, wherein the attachment means comprises a clamp.

83. Apparatus as claimed in any of claim 76, wherein the attachment means comprises a clip.

84. Apparatus as claimed in claim 76, wherein the hook means is movable relative to the attachment means to selectively disassociate the hook means from the attachment means.

85. A device as claimed in claim 84, wherein the attachment means defines a groove in which the hook means is slidable to selectively disassociate the hook means from the attachment means.

86. Apparatus for delivery of medicament to the respiratory system comprising:

a medication cup that is adapted to hold a liquid medication to be delivered to a respiratory system;

an aerosol generator;

a housing for the aerosol generator;

a liquid supplier that is adapted to deliver the liquid medicament from the cup to the aerosol generator; and a connector through which aerosol generated by the aerosol generator is delivered, wherein the liquid supplier is releasably mounted to the generator housing with a plurality of fingers for snap-fit engagement.

87. Apparatus for delivery of medicament to the respiratory system comprising:

a medication cup that is adapted to hold a liquid medication to be delivered to a respiratory system;

an aerosol generator;

a housing for the aerosol generator;

a liquid supplier that is adapted to deliver the liquid medicament from the cup to the aerosol generator, wherein the liquid supplier is releasably mounted to the aerosol generator housing with a plurality of fingers for snap-fit engagement; and a connector through which aerosol generated by the aerosol generator is delivered;

wherein the aerosol generator housing has signal connection means for connection to a control means to control the operation of the aerosol generator.

88. Apparatus for delivery of medicament to the respiratory system comprising:

a medication cup that is adapted to hold a liquid medication to be delivered to a respiratory system;

an aerosol generator;

a housing for the aerosol generator;

a liquid supplier that is adapted to deliver the liquid medicament from the cup to the aerosol generator, wherein the liquid supplier is releasably mounted to the aerosol generator housing with a plurality of fingers for snap-fit engagement; and a connector through which aerosol generated by the aerosol generator is delivered, wherein the medication cup is releasably mounted to the aerosol generator housing.

* * * * *